US011156621B2

(12) United States Patent
Otvos et al.

(10) Patent No.: US 11,156,621 B2
(45) Date of Patent: Oct. 26, 2021

(54) MULTI-PARAMETER METABOLIC VULNERABILITY INDEX EVALUATIONS

(71) Applicant: LipoScience, Inc., Morrisville, NC (US)

(72) Inventors: James D. Otvos, Cary, NC (US); Irina Y. Shalaurova, Cary, NC (US)

(73) Assignee: LipoScience, Inc., Morrisville, NC (US)

( * ) Notice: Subject to any disclaimer, the term of this patent is extended or adjusted under 35 U.S.C. 154(b) by 413 days.

(21) Appl. No.: 16/124,886

(22) Filed: Sep. 7, 2018

(65) Prior Publication Data
US 2019/0072572 A1    Mar. 7, 2019

Related U.S. Application Data

(60) Provisional application No. 62/619,497, filed on Jan. 19, 2018, provisional application No. 62/555,421, filed on Sep. 7, 2017.

(51) Int. Cl.
*G01N 33/92* (2006.01)
*G01R 33/465* (2006.01)
(Continued)

(52) U.S. Cl.
CPC .......... *G01N 33/92* (2013.01); *A61B 5/055* (2013.01); *A61B 5/7275* (2013.01); *G01R 33/465* (2013.01); *G16H 10/40* (2018.01); *G16H 50/30* (2018.01); *G16H 50/50* (2018.01); *G16Z 99/00* (2019.02); *G01N 2800/32* (2013.01); *G16B 20/00* (2019.02); *G16C 20/20* (2019.02)

(58) Field of Classification Search
CPC ....................................................... G01N 33/92
USPC ......................................................... 436/71
See application file for complete search history.

(56) References Cited

U.S. PATENT DOCUMENTS 4,933,844 A * 6/1990 Otvos .................. G01R 33/465
                                                      128/922
5,343,389 A * 8/1994 Otvos .................... G01N 33/92
                                                      436/173
(Continued)

FOREIGN PATENT DOCUMENTS

WO        2013/185014 A1    12/2013

OTHER PUBLICATIONS

Baker, J. et al., "High-density lipoprotein particles and markers of inflammation and thrombotic activity in patients with untreated HIV infection," The Journal of Infectious Diseases 201(2):285-292 (2010).
(Continued)

*Primary Examiner* — Arlen Soderquist
(74) *Attorney, Agent, or Firm* — Kilpatrick Townsend & Stockton LLP

(57) ABSTRACT

Disclosed are methods and systems to determine a subject's metabolic vulnerability index (MVX) score using at least one defined mathematical model of risk. The methods comprise evaluating various biomarkers to distinguish various health risks. In one embodiment, the method comprises evaluating biomarkers to determine a relative risk of premature all-cause mortality. The model may include NMR-derived measurements of GlycA, S-HDLP, branched chain amino acids (BCAAs), ketone bodies, total serum protein, and citrate in at least one biosample of the subject.

29 Claims, 16 Drawing Sheets

(51) Int. Cl.
*G16H 10/40* (2018.01)
*G16H 50/30* (2018.01)
*A61B 5/055* (2006.01)
*G16H 50/50* (2018.01)
*A61B 5/00* (2006.01)
*G16Z 99/00* (2019.01)
*G16B 20/00* (2019.01)
*G16C 20/20* (2019.01)

(56) References Cited

U.S. PATENT DOCUMENTS

| | | | | |
|---|---|---|---|---|
| 6,284,219 B1* | 9/2001 | Ajami | | A61K 51/1206 424/1.11 |
| 6,518,069 B1* | 2/2003 | Otvos | | G01N 33/66 436/173 |
| 6,576,471 B2* | 6/2003 | Otvos | | G01N 33/92 436/71 |
| 6,653,140 B2* | 11/2003 | Otvos | | G01N 33/92 436/13 |
| 7,790,465 B2* | 9/2010 | Otvos | | G01N 33/6893 436/71 |
| 8,005,623 B2* | 8/2011 | Hellerstein | | G01N 33/5014 702/19 |
| 8,013,602 B2* | 9/2011 | Otvos | | G01R 33/465 324/309 |
| 8,663,602 B2* | 3/2014 | Hellerstein | | G01N 33/60 424/9.2 |
| 8,704,521 B2* | 4/2014 | Otvos | | G01R 33/307 324/318 |
| 8,849,577 B2* | 9/2014 | Ryals | | G01N 33/5008 702/19 |
| 9,057,736 B2* | 6/2015 | Urdea | | G01N 33/6845 |
| 9,361,429 B2* | 6/2016 | Otvos | | G16H 50/50 |
| 9,435,870 B2* | 9/2016 | Otvos | | G01R 33/465 |
| 9,470,771 B2* | 10/2016 | Otvos | | G01N 33/49 |
| 9,483,611 B2* | 11/2016 | Otvos | | G06F 19/00 |
| 9,483,612 B2* | 11/2016 | Otvos | | G01N 33/92 |
| 9,792,410 B2* | 10/2017 | Otvos | | G16H 20/10 |
| 9,952,232 B2* | 4/2018 | Otvos | | G01R 33/465 |
| 10,365,339 B2* | 7/2019 | Otvos | | G01R 33/307 |
| 10,386,355 B2* | 8/2019 | Otvos | | G01N 33/487 |
| 10,388,414 B2* | 8/2019 | Otvos | | A61B 5/7275 |
| 10,852,293 B2* | 12/2020 | Otvos | | G01N 24/08 |
| 2002/0087276 A1* | 7/2002 | Otvos | | G01N 33/92 702/24 |
| 2003/0119194 A1* | 6/2003 | Otvos | | G01N 33/92 436/71 |
| 2004/0048253 A1* | 3/2004 | Panzer | | C07H 21/04 435/6.16 |
| 2006/0183234 A1* | 8/2006 | Otvos | | G01N 33/92 436/71 |
| 2007/0264677 A1* | 11/2007 | Otvos | | G16H 10/40 435/11 |
| 2008/0161228 A1* | 7/2008 | Ryals | | G01N 33/5008 702/19 |
| 2011/0295517 A1* | 12/2011 | Otvos | | G01R 33/307 702/19 |
| 2013/0289884 A1* | 10/2013 | Otvos | | G16H 50/50 702/19 |
| 2013/0289885 A1* | 10/2013 | Otvos | | G01N 33/487 702/19 |
| 2013/0328561 A1* | 12/2013 | Otvos | | G16H 50/30 324/309 |
| 2013/0332082 A1* | 12/2013 | Otvos | | G06F 17/10 702/19 |
| 2014/0161721 A1* | 6/2014 | Hatchwell | | C12Q 1/6883 424/1.49 |
| 2016/0032363 A1* | 2/2016 | Stintzi | | C12Q 1/6883 514/503 |
| 2016/0077116 A1* | 3/2016 | Otvos | | G01R 33/465 506/12 |

OTHER PUBLICATIONS

Laaksonen, R., "Identifying new risk markers and potential targets for coronary artery disease: the value of the lipidome and metabolome," Cardiovasc. Drugs Ther. 30(1):19-32 (2016).
PCT/US2018/049951, "International Search Report and Written Opinion," dated Jan. 21, 2019, 18 pages.
PCT/US2018/049951, "Invitation to Pay Additional Fees and, Where Applicable, Protest Fee," dated Nov. 28, 2018, 13 pages.
White, S. L. et al., "Metabolic profiling of gestational diabetes in obese women during pregnancy," Diabetologia 60(10):1903-1912 (2017).
PCT/US2018/049951 , "International Preliminary Report on Patentability", dated Mar. 19, 2020, 12 pages.

* cited by examiner

Cox Model for All-Cause Mortality in CATHGEN
5-Year Follow-up (1259 deaths/6938 subjects)

| Parameter | β-coefficient | $\chi^2$ | P |
|---|---|---|---|
| Age | 0.03037 | 126.2 | <0.0001 |
| African American | 0.04042 | 0.3 | 0.60 |
| Hispanic | 0.19024 | 1.3 | 0.26 |
| Asian | 0.23033 | 1.8 | 0.18 |
| Gender | 0.39474 | 37.0 | <0.0001 |
| Smoking | 0.21655 | 13.8 | 0.0002 |
| Hypertension | -0.26803 | 18.9 | <0.0001 |
| Diabetes | 0.37845 | 36.5 | <0.0001 |
| BMI | -0.01034 | 5.2 | 0.02 |
| TRLP | 0.00149 | 13.1 | 0.0003 |
| LDLP | -0.00009 | 1.6 | 0.21 |
| GlycA* | 1.52946 | 123.8 | <0.0001 |
| S-HDLP* | -1.11419 | 179.5 | <0.0001 |
| BCAA* | -1.09817 | 87.1 | <0.0001 |
| Ketone Bodies* | 0.11065 | 6.0 | 0.01 |
| Citrate* | 0.64418 | 53.6 | <0.0001 |
| Protein* | -0.95921 | 42.4 | <0.0001 |

*Values are natural log-transformed

Inflammation (INFX): GlycA*, S-HDLP*
Metabolic Malnutrition (MMX): BCAA*, Ketone Bodies*, Citrate*, Protein*

Figure 4

Metabolic Vulnerability Index (MVX) =
Inflammation Index (INFX) + Metabolic Malnutrition Index (MMX)

Cox Models for Mortality During 5-Year Follow-up in CATHGEN

| Parameter | β-coefficient | χ² | p | Parameter | β-coefficient | χ² | p |
|---|---|---|---|---|---|---|---|
| Age | 0.03072 | 132.0 | <0.0001 | Age | 0.03089 | 136.5 | <0.0001 |
| African American | 0.05276 | 0.5 | 0.48 | African American | 0.05263 | 0.5 | 0.48 |
| Hispanic | 0.17375 | 1.1 | 0.30 | Hispanic | 0.16905 | 1.0 | 0.32 |
| Asian | 0.24679 | 2.1 | 0.15 | Asian | 0.24755 | 2.1 | 0.15 |
| Gender | 0.37149 | 34.5 | <0.0001 | Gender | 0.36498 | 35.2 | <0.0001 |
| Smoking | 0.19479 | 11.2 | 0.0008 | Smoking | 0.19270 | 11.1 | 0.0009 |
| Hypertension | -0.24552 | 15.9 | <0.0001 | Hypertension | -0.24597 | 16.0 | <0.0001 |
| Diabetes | 0.36886 | 34.8 | <0.0001 | Diabetes | 0.36712 | 34.6 | <0.0001 |
| BMI | -0.01052 | 5.7 | 0.02 | BMI | -0.01070 | 6.0 | 0.01 |
| TRLP | 0.00207 | 26.7 | <0.0001 | TRLP | 0.00205 | 26.5 | <0.0001 |
| LDLP | -0.00007 | 0.9 | 0.34 | LDLP | -0.00007 | 0.9 | 0.34 |
| INFX | 0.84142 | 437.9 | <0.0001 | MVX | 1.04761 | 920.4 | <0.0001 |
| MMX | 1.07716 | 204.8 | <0.0001 | | | | |

Figure 5

Cox Models for Prediction of Short-term and Longer-term Mortality by MVX Score in CATHGEN

| Parameter | 1-Year Follow-up (336 deaths/6938 subjects) | | | Full Follow-up (mean 7 yrs) (1874 deaths/6938 subjects) | | |
|---|---|---|---|---|---|---|
| | β-coeff. | χ² | P | β-coeff. | χ² | P |
| Age | 0.02430 | 24.7 | <0.0001 | 0.03526 | 248.5 | <0.0001 |
| Afr American | 0.13031 | 0.9 | 0.35 | 0.04987 | 0.7 | 0.42 |
| Hispanic | -0.02756 | 0.0 | 0.94 | 0.04832 | 0.1 | 0.73 |
| Asian | -0.09740 | 0.1 | 0.79 | 0.03297 | 0.0 | 0.83 |
| Gender | 0.55491 | 21.3 | <0.0001 | 0.34600 | 46.8 | <0.0001 |
| Smoking | 0.00051 | 0.0 | 0.99 | 0.22741 | 22.9 | <0.0001 |
| Hypertension | -0.29396 | 6.2 | 0.01 | -0.16268 | 10.2 | 0.001 |
| Diabetes | 0.35695 | 8.7 | 0.003 | 0.32260 | 39.4 | <0.0001 |
| BMI | -0.01982 | 5.3 | 0.02 | -0.00735 | 4.2 | 0.04 |
| TRLP | 0.00090 | 1.2 | 0.27 | 0.00171 | 26.0 | <0.0001 |
| LDLP | 0.00005 | 0.2 | 0.69 | -0.00006 | 0.9 | 0.34 |
| MVX | 1.18529 | 451.2 | <0.0001 | 0.96517 | 973.8 | <0.0001 |

Figure 6

Relative Strength of Mortality Risk Prediction* in CATHGEN Over 3 Time Intervals by MVX Alone Compared to a Model Also Including Age, Gender, and Other Risk Factors.

| Model Parameters | 1-Year Follow-up (336 deaths/6936) | 5-Year Follow-up (1259 deaths/6936) | Full Follow-up (1873 deaths/6936) |
|---|---|---|---|
| MVX Alone | 374 | 794 | 886 |
| MVX + 9 Covariates | 446 | 1071 | 1323 |

*Values given are the likelihood ratio chi-square statistic of the indicated Cox models, providing a measure of the predictive strength of MVX alone compared to a more complex model that adds age, race, gender, smoking, hypertension, diabetes, BMI, TRLP, and LDLP. TRLP = triglyceride-rich lipoprotein particles; LDLP = LDL particles.

Figure 7

Logistic Regression for CVD and Mortality Outcomes in MESA

←——— Composite CVD Outcome ———→

| Parameter | | Nonfatal CVD Survived n=432 $\chi^2$ | P | | Nonfatal CVD Died Later n=128 $\chi^2$ | P | | Fatal CVD n=225 $\chi^2$ | P | | Non-CVD Death n=610 $\chi^2$ | P |
|---|---|---|---|---|---|---|---|---|---|---|---|---|
| Age | + | 35.6 | <0.0001 | + | 75.6 | <0.0001 | + | 179.2 | <0.0001 | + | 356.2 | <0.0001 |
| AfrAmer | - | 17.2 | <0.0001 | - | 4.6 | 0.03 | - | 0.0 | 0.87 | - | 0.8 | 0.37 |
| Hisp | - | 6.3 | 0.01 | - | 2.6 | 0.11 | - | 2.1 | 0.14 | - | 5.6 | 0.02 |
| Asian | - | 5.5 | 0.02 | - | 2.9 | 0.09 | - | 1.5 | 0.21 | - | 1.6 | 0.21 |
| Gender | + | 30.0 | <0.0001 | + | 41.6 | <0.0001 | + | 30.5 | <0.0001 | + | 59.1 | <0.0001 |
| Smoking | + | 9.4 | 0.002 | + | 13.7 | 0.0002 | + | 16.4 | <0.0001 | + | 55.0 | <0.0001 |
| SBP | + | 36.2 | <0.0001 | + | 10.5 | 0.001 | + | 18.3 | <0.0001 | + | 0.8 | 0.37 |
| Diabetes | + | 31.4 | <0.0001 | + | 13.8 | 0.0002 | + | 17.9 | <0.0001 | + | 16.5 | <0.0001 |
| BMI | + | 3.9 | 0.05 | + | 0.4 | 0.52 | + | 6.5 | 0.012 | + | 6.4 | 0.01 |
| TC/HDL-C | + | 12.1 | 0.0005 | - | 1.2 | 0.27 | - | 2.4 | 0.12 | - | 4.6 | 0.03 |
| MVX | + | 0.5 | 0.50 | + | 28.9 | <0.0001 | + | 29.0 | <0.0001 | + | 78.4 | <0.0001 |

From multinomial logistic regression analysis for CVD and mortality outcomes during mean 11-year follow-up, with No CVD, No Death as the reference category (n=5344).

Figure 9

Logistic Regression for CHF and Mortality Outcomes in MESA

| Parameter | CHF(+) Death(-) n=137 | | | CHF(+) Death(+) n=140 | | | CHF(-) Death(+) n=823 | | |
|---|---|---|---|---|---|---|---|---|---|
| | | $\chi^2$ | P | | $\chi^2$ | P | | $\chi^2$ | P |
| Age | + | 24.6 | <0.0001 | + | 102.3 | <0.0001 | + | 449.2 | <0.0001 |
| AfrAmer | - | 5.6 | 0.02 | - | 1.5 | 0.22 | - | 0.4 | 0.51 |
| Hisp | - | 7.0 | 0.008 | - | 2.8 | 0.09 | - | 6.5 | 0.01 |
| Asian | - | 0.9 | 0.34 | - | 2.3 | 0.13 | - | 2.1 | 0.14 |
| Gender | + | 14.1 | 0.0002 | + | 37.6 | <0.0001 | + | 73.4 | <0.0001 |
| Smoking | + | 5.3 | 0.02 | + | 5.6 | 0.02 | + | 66.9 | <0.0001 |
| SBP | + | 19.4 | <0.0001 | + | 8.8 | 0.003 | + | 4.9 | 0.03 |
| Diabetes | + | 17.6 | 0.0003 | + | 30.8 | <0.0001 | + | 15.8 | <0.0001 |
| BMI | + | 14.0 | 0.0002 | + | 12.3 | 0.0004 | + | 5.7 | 0.02 |
| TC/HDL-C | - | 4.3 | 0.04 | + | 0.7 | 0.39 | - | 6.7 | 0.01 |
| MVX | + | 3.2 | 0.41 | + | 56.3 | <0.0001 | + | 83.4 | <0.0001 |

From multinomial logistic regression analysis for dual CVD and mortality outcomes during mean 11-year follow-up, with CHF(-) Death(-) as the reference category (n=5639).

Figure 10

Logistic Regression for Cancer and Mortality Outcomes in MESA

| Parameter | Cancer(+) Death(-) n=219 | | | Cancer(+) Death(+) n=221 | | | Cancer(-) Death(+) n=607 | | |
|---|---|---|---|---|---|---|---|---|---|
| | | $\chi^2$ | P | | $\chi^2$ | P | | $\chi^2$ | P |
| Age | + | 30.4 | <0.0001 | + | 150.6 | <0.0001 | + | 337.6 | <0.0001 |
| AfrAmer | - | 0.5 | 0.47 | + | 0.0 | 0.96 | - | 0.4 | 0.52 |
| Hisp | - | 9.0 | 0.003 | - | 5.2 | 0.02 | - | 4.1 | 0.04 |
| Asian | - | 8.0 | 0.005 | - | 0.5 | 0.47 | - | 2.8 | 0.09 |
| Gender | + | 11.5 | 0.0007 | + | 47.5 | <0.0001 | + | 50.1 | <0.0001 |
| Smoking | + | 0.7 | 0.40 | + | 20.7 | <0.0001 | + | 34.0 | <0.0001 |
| SBP | + | 2.7 | 0.10 | + | 0.1 | 0.71 | + | 6.6 | 0.01 |
| Diabetes | + | 0.1 | 0.73 | + | 3.5 | 0.06 | + | 26.5 | <0.0001 |
| BMI | + | 1.2 | 0.27 | + | 6.4 | 0.01 | + | 5.7 | 0.02 |
| TC/HDL-C | - | 0.2 | 0.70 | - | 2.5 | 0.11 | - | 0.7 | 0.41 |
| MVX | + | 1.8 | 0.18 | + | 55.7 | <0.0001 | + | 70.3 | <0.0001 |

From multinomial logistic regression analysis for dual CVD and mortality outcomes during mean 7-year follow-up, with Cancer(-) Death(-) as the reference category (n=4626).

Figure 11

Logistic Regression for CKD and Mortality Outcomes in MESA

| Parameter | | CKD(+) Death(-) n=76 | | | CKD(+) Death(+) n=105 | | | CKD(-) Death(+) n=723 | |
|---|---|---|---|---|---|---|---|---|---|
| | | $\chi^2$ | P | | $\chi^2$ | P | | $\chi^2$ | P |
| Age | + | 21.4 | <0.0001 | + | 85.6 | <0.0001 | + | 377.4 | <0.0001 |
| AfrAmer | + | 0.9 | 0.35 | - | 0.1 | 0.78 | - | 0.1 | 0.79 |
| Hisp | + | 1.5 | 0.22 | - | 0.1 | 0.82 | - | 5.6 | 0.02 |
| Asian | + | 0.1 | 0.71 | - | 0.0 | 0.89 | - | 2.1 | 0.15 |
| Gender | + | 20.3 | <0.0001 | + | 30.9 | <0.0001 | + | 64.7 | <0.0001 |
| Smoking | - | 0.0 | 0.92 | - | 0.0 | 0.97 | + | 51.5 | <0.0001 |
| SBP | + | 13.1 | 0.0003 | + | 4.3 | 0.04 | + | 4.1 | 0.04 |
| Diabetes | + | 6.4 | 0.01 | + | 24.9 | <0.0001 | + | 17.1 | <0.0001 |
| BMI | + | 5.3 | 0.02 | + | 12.9 | 0.0003 | + | 5.7 | 0.02 |
| TC/HDL-C | - | 0.6 | 0.42 | - | 3.3 | 0.07 | - | 5.0 | 0.02 |
| MVX | + | 10.8 | 0.001 | + | 59.9 | <0.0001 | + | 77.9 | <0.0001 |

From multinomial logistic regression analysis for dual CVD and mortality outcomes during mean 7-year follow-up, with CKD(-) Death(-) as the reference category (n=4769).

Figure 12

Models for Calculation of MVX and Related Multimarkers*

INFX = 25 + (lnGlycA * -3.01437) + (lnS-HDLP * -12.18031) + (lnGlycA * lnS-HDLP * 1.75599)

MMX1 = 10 + (lnBCAA * -1.10056) + (lnKetone Bodies * 0.2378)

MMX2 = 45 + (lnCitrate * -7.54332) + (lnProtein * -7.0407) + (lnCitrate * lnProtein * 1.32706)

MMX = (MMX1 * 0.70456) + (MMX2 * 1.0)

For application to normal-risk patient populations (ie., MESA)

MVX1 = (INFX * 0.84310) + (MMX1 * 1.0)

For application to high-risk patient populations (ie., CATHGEN)

MVX = (INFX * 0.81524) + (MMX * 1.0)

*For clinical use, each multimarker can be transformed into a numerical score (1-100)

Figure 16

MULTI-PARAMETER METABOLIC VULNERABILITY INDEX EVALUATIONS

RELATED PATENT APPLICATIONS

This patent application claims the benefit of U.S. provisional patent application No. 62/555,421 filed on Sep. 7, 2017, entitled METHODS AND SYSTEMS FOR MEASURING PVX, and U.S. provisional patent application No. 62/619,497 filed on Jan. 19, 2018, entitled MULTI-PARAMETER METABOLIC VULNERABILITY INDEX EVALUATIONS. The entire content of the foregoing applications is incorporated herein by reference, including all text, tables, and drawings.

FIELD

The present disclosure relates generally to analysis of in vitro biosamples. The disclosure may be particularly suitable for NMR analysis of in vitro biosamples.

BACKGROUND

Cardiovascular disease (CVD)-related death is considered to be the most severe outcome of prolonged exposure to "traditional" CVD risk factors. These risk factors, extensively studied and documented in the Framingham Offspring study, include age, gender, blood pressure, smoking habits, and cholesterol values. See Wilson et al., *Impact of National Guidelines for Cholesterol Risk Factor Screening, The Framingham Offspring Study*, JAMA, 1989; 262: 41-44. These factors have long been used to differentiate normative populations and populations at risk of suffering from a CVD-associated event.

Typically a patient's overall risk of coronary heart disease (CHD) and/or CVD is initially assessed based on measurements of cholesterol content of a patient's LDL and HDL particles, denoted as LDL cholesterol (LDL-C) and HDL cholesterol (HDL-C), rather than the numbers of these particles. Treatment decisions are often made with the goal of reducing the "bad" cholesterol (LDL-C) and/or increasing the "good" cholesterol (HDL-C) with a secondary focus on optimizing modifiable Framingham risk factors.

Risk calculations based on these Framingham factors are generally able to predict the incidence of CVD-associated events. However, these risk calculators are developed to predict a composite CVD outcome composed of both non-fatal and fatal CVD events. Additionally, clinical trials typically use composite CVD outcomes as study endpoints. Analysis of recent clinical trials has shown heterogeneous drug effects on the fatal and non-fatal components of the composite CVD endpoints. While, for example, LDL-lowering drugs in some trials reduced the incidence of a composite CVD endpoint and the non-fatal event component of that endpoint, the same drugs failed to reduce the fatal CVD event component of the combined endpoint, or all-cause mortality. Conversely, some diabetes drugs reduced the composite CVD endpoints by only reducing CVD death and all-cause mortality, not non-fatal CVD events. The results of these studies indicate that the determinants of fatal and non-fatal CVD events could be different, making reliance on composite CVD outcomes potentially problematic.

Traditional CVD risk calculators fail to take into account the complex pathophysiology of various disease states, and some traditional CVD risk factors are often paradoxically associated with survival in malnourished, chronically ill patients. For example, in patients with chronic cardiac and kidney disease, those with higher body mass indices, higher serum cholesterol levels, and higher blood pressure have increased survival rates. See Kalantar-Zadeh et al., *Reverse Epidemiology of Conventional Cardiovascular Risk Factors in Patients with Chronic Heart Failure*, J. Am. College Cardiology, 2004; 42: 1439-44. This calls into question clinical reliance on Framingham risk factors, regardless of disease state, to determine a patient's risk of morbidity and mortality.

In light of the fact that clinicians currently rely on traditional CVD risk factors from risk calculators based on composite outcomes to predict patient prognoses, there remains a need for risk calculators comprised of factors that can better predict or assess a person's risk of premature death from any cause as opposed to the risk of suffering a non-fatal event.

SUMMARY

Embodiments of the disclosure include methods and systems that evaluate a person's relative risk of premature all-cause mortality and/or provide mortality risk stratification by evaluating NMR spectra of an in vitro blood plasma or serum patient sample using a defined multi-component risk assessment model to determine a patient's Metabolic Vulnerability Index (MVX) score.

The MVX score may be calculated using a plurality of NMR derived measurements including: high-density lipoprotein (HDL) subclasses such as small HDL particles (S-HDLP), the inflammation marker GlycA, one or more branched-chain amino acids (valine, leucine, and/or isoleucine), one or more ketone bodies (beta-hydroxybutyrate, acetoacetate, and/or acetone), and optionally citrate (Citrate) and/or a measure of serum protein (Protein). In an embodiment, the HDLP subclass is small HDL particles (S-HDLP).

Embodiments of the disclosure include methods of determining the levels of markers associated with a person's risk of premature death. The methods may include obtaining a sample from the person and measuring GlycA, at least one high density lipoprotein particle (HDLP) subclass, at least one branched chain amino acid (BCAA), at least one ketone body. In an embodiment the high density lipoprotein particle is a small HDL particles (S-HDLP). In some embodiments, these measurements are used to generate a MVX score. In some embodiments, the MVX score is determined by using the following model: $MVX = A + \beta_1 * \ln GlycA + \beta_2 * \ln S\text{-}HDLP + \beta_4 * \ln BCAA + \beta_5 * \ln KetoneBody$. In some embodiments, the MVX value is determined by using the following model: $MVX = A + \beta_1 * \ln GlycA + \beta_2 * \ln S\text{-}HDLP + \beta_3 * (\ln GlycA * \ln S\text{-}HDLP) + \beta_4 * \ln BCAA + \beta_5 * \ln KetoneBody$.

It is noted that throughout this disclosure, the empirical values for A and $\beta_1$-$\beta_n$ may vary depending upon the model used. For example, $\beta_1$ in the first above formula for MVX (i.e., the formula that does not include the term $\beta_3 * (\ln GlycA * \ln S\text{-}HDLP)$), will generally be a different value than $\beta_1$ in the second above formula (i.e., the equation that does include that product term), respectively.

In some embodiments, the methods include measuring at least one of citrate and protein in addition to GlycA, at least one HDLP subclass, at least one BCAA, and at least one ketone body. In some embodiments, the measuring that includes at least one of citrate (Citrate) and serum protein (Protein) is performed on a subject deemed to be at high risk for CVD-related death. In some embodiments, the MVX value is determined using the following model: $MVX = A + \beta_1 * \ln GlycA + \beta_2 * \ln S\text{-}HDLP + \beta_3 * (\ln GlycA * \ln S\text{-}HDLP) +$ $\beta 4*\ln BCAA+\beta 5*\ln KetoneBody+\beta 6*\ln Citrate+\beta 7*\ln Protein+\beta 8*(\ln Citrate*\ln Protein)$.

In some embodiments, the MVX value is defined as comprising an inflammation index (INFX) value and a metabolic malnutrition index (MMX) value. In some embodiments, the measurements of at least GlycA and the at least one HDLP subclass are used to generate an inflammation index (INFX) value. In some embodiments, the INFX value is determined using the following model: $INFX=\beta 1*\ln GlycA+\beta 2*\ln S\text{-}HDLP+\beta 3*(\ln GlycA*\ln S\text{-}HDLP)$.

In some embodiments, the measurements of at least one BCAA and at least one ketone body are used to generate a metabolic malnutrition index (MMX) value. In some embodiments, the MMX value is determined using the following model: $MMX=\beta 4*\ln BCAA+\beta 5*\ln KetoneBody$. This model may be denoted MMX1 and, as discussed in detail herein, be the calculation used for populations/subjects that are believed to be low-risk (e.g., have not had a known cardiovascular (CV) event).

In other embodiments, the measurements of at least one BCAA, at least one ketone body, citrate, and protein are used to generate an alternate MMX value. For example, in some embodiments, the MMX value may be determined using the following model: $MMX=\beta 4*\ln BCAA+\beta 5*\ln KetoneBody+\beta 6*\ln Citrate+\beta 7*\ln Protein$. Or, the MMX value may be determined using the following model: $MMX=\beta 4*\ln BCAA+\beta 5*\ln KetoneBody+\beta 6*\ln Citrate+\beta 7*\ln Protein+\beta 8*(\ln Citrate*\ln Protein)$. In such embodiments, MMX may be described as follows: $MMX=\beta 9*MMX1+\beta 10*MMX2$, where MMX1 is as described above, and $MMX2=\beta 6*\ln Citrate+\beta 7*\ln Protein+\beta 8*(\ln Citrate*\ln Protein)$.

The measurements used to generate the MMX value including measurements of citrate and protein are generally performed in a subject and/or population deemed to be at high risk for CVD-related death (e.g. subjects who have had a cardiovascular event or symptoms suggestive of underlying CVD).

Thus, in some embodiments, the metabolic vulnerability index may be described as: $MVX=\beta i*INFX+\beta m*MMX$. For application to normal (i.e., low) risk patient populations (e.g., people who have not had a known CV event) the metabolic vulnerability index may be described as $MVX1=\beta i*INFX+\beta m*MMX1$ (wherein $\beta i$ and $\beta m$ may have unique values depending upon the model used). Conversely, for application to high-risk patient populations (e.g., people who have had a known CV event) the metabolic vulnerability index may be described as $MVX=\beta i*INFX+\beta m*MMX$ wherein $\beta i$ and $\beta m$ may have unique values depending upon the model used and $MMX=\beta 9*MMX1+\beta 10*MMX2$. In some cases $\beta m$ is the same for both the low-risk and the high-risk models (see e.g., FIG. 16).

For example, in some cases the MVX score may be monitored in a high-risk subject or population as a way to monitor the subject's overall health and risk for a fatal CV event or death from other causes. Or, the MVX score may be monitored in a clinical trial for a new pharmaceutical that is being performed in a high-risk population as a way to monitor the efficacy of the test drug. For low-risk subjects, the clinician may choose to monitor the MVX1 value as a means to assess general health and wellness. The MVX1 value may, in certain embodiments, be used as a guide to lifestyle changes that promote cardiac health. Still other embodiments are directed to a system. The system includes an NMR spectrometer for acquiring at least one NMR spectrum of an in vitro biosample and at least one processor in communication with the NMR spectrometer. The at least one processor may be configured to determine for a respective biosample using the at least one NMR spectrum a metabolic vulnerability index score based on at least one defined mathematical model of risk of premature mortality that may consider at least one HDL subclass component measurement, at least one branched chain amino acid measurement, at least one ketone body measurement, a GlycA measurement, and optionally a citrate measurement and/or a protein measurement obtained from at least one in vitro biosample of the subject. In an embodiment, the HDLP subclass is small HDLP (S-HDLP). In some embodiments, the processor may be configured to calculate an MVX score based on the measurements of GlycA, at least one ketone body, at least one branched chain amino acid, and the at least one of the HDLP subclass using the following formula: $MVX=A+\beta 1*\ln GlycA+\beta 2*\ln S\text{-}HDLP+\beta 4*\ln BCAA+\beta 5*\ln KetoneBody$. In some embodiments, the processor may be configured to calculate the MVX score using the following model: $MVX=A+\beta 1*\ln GlycA+\beta 2*\ln S\text{-}HDLP+\beta 3*(\ln GlycA*\ln S\text{-}HDLP)+\beta 4*\ln BCAA+\beta 5*\ln KetoneBody$. In some embodiments, the processor may be configured to calculate an MVX score using the following model: $MVX=A+\beta 1*\ln GlycA+\beta 2*\ln S\text{-}HDLP+\beta 3*(\ln GlycA*\ln S\text{-}HDLP)+\beta 4*\ln BCAA+\beta 5*\ln KetoneBody+\beta 6*\ln Citrate+\beta 7*\ln Protein+\beta 8*(\ln Citrate*\ln Protein)$. In some embodiments, the processor may be configured to calculate an MVX score comprising an inflammation index (INFX) value and a metabolic malnutrition index (MMX) value. Thus, in some embodiments, the processor may be configured to calculate an MVX score based on the following model: $MVX=\beta i*INFX+\beta m*MMX$. In these embodiments, the processor may be configured to calculate an INFX value using the following model: $INFX=\beta 1*\ln GlycA+\beta 2*\ln S\text{-}HDLP+\beta 3*(\ln GlycA*\ln S\text{-}HDLP)$. In some embodiments, the processor may be configured to calculate an MMX value using the following model: $MMX=\beta 4*\ln BCAA+\beta 5*\ln KetoneBody$; this model may be denoted MMX1. In some embodiments, the processor may be configured to calculate an MMX using the following model: $MMX=\beta 4*\ln BCAA+\beta 5*\ln KetoneBody+\beta 6*\ln Citrate+\beta 7*\ln Protein$. In another embodiment, the processor may be configured to calculate the MMX using the following model: $MMX=\beta 4*\ln BCAA+\beta 5*\ln KetoneBody+\beta 6*\ln Citrate+\beta 7*\ln Protein+\beta 8*(\ln Citrate*\ln Protein)$. In such embodiments, MMX may be described as follows: $MMX=\beta 9*MMX1+\beta 10*MMX2$, where MMX1 is as described above, and $MMX2=\beta 6*\ln Citrate+\beta 7*\ln Protein+\beta 8*(\ln Citrate*\ln Protein)$.

Still other embodiments are directed to NMR systems. The systems include a NMR spectrometer; a flow probe in communication with the spectrometer; and at least one processor in communication with the spectrometer. The at least one processor may be configured to obtain (i) at least one NMR signal of a defined GlycA fitting region of NMR spectra associated with GlycA of a blood plasma or serum specimen in the flow probe; (ii) at least one NMR signal of a defined ketone body fitting region of NMR spectra associated with the specimen in the flow probe; (iii) at least one NMR signal of a defined BCAA fitting region of NMR spectra associated with the specimen in the flow probe; and (iv) at least one NMR signal of HDLP subclass parameters. The processor may be further configured to calculate measurements of the GlycA, the at least one ketone body, the at least one branched chain amino acid, and the HDLP subclass parameters. The system may be further configured to calculate a MVX score using a defined mathematical model of risk of all cause-mortality that uses the calculated measurements of GlycA, at least one ketone body, at least one branched chain amino acid, at least one of the HDLP subclass parameters, and optionally serum protein (Protein) and/or citrate (Citrate). In an embodiment, the HDLP subclass is small HDLP (S-HDLP). In some embodiments, the system may be further configured to calculate an MVX score based on the measurements of GlycA, at least one ketone body, at least one branched chain amino acid, and the at least one of the HDLP subclass using the following formula: MVX=A+$\beta 1$*lnGlycA+$\beta 2$*lnS-HDLP+$\beta 4$*lnBCAA+$\beta 5$*lnKetoneBody. In some embodiments, the system may be further configured to calculate the MVX score using the following model: MVX=A+$\beta 1$*lnGlycA+$\beta 2$*lnS-HDLP+$\beta 3$*(lnGlycA*lnS-HDLP)+$\beta 4$*lnBCAA+$\beta 5$*lnKetoneBody. In some embodiments, the system may be further configured to calculate an MVX score using the following model: MVX=A+$\beta 1$*lnGlycA+$\beta 2$*lnS-HDLP+$\beta 3$*(lnGlycA*lnS-HDLP)+$\beta 4$*lnBCAA+$\beta 5$*lnKetoneBody+$\beta 6$*lnCitrate+$\beta 7$*lnProtein+$\beta 8$*(lnCitrate*lnProtein). In some embodiments, the system may be further configured to calculate an MVX score comprising an inflammation index (INFX) value and a metabolic malnutrition index (MMX) value. Thus, in some embodiments, the system may be further configured to calculate an MVX score based on the following model: MVX=$\beta i$*INFX+$\beta m$*MMX. In these embodiments, the system may be further configured to calculate an INFX value using the following model: INFX=$\beta 1$*lnGlycA+$\beta 2$*lnS-HDLP+$\beta 3$*(lnGlycA*lnS-HDLP). In some embodiments, the system may be further configured to calculate an MMX value using the following model: MMX=$\beta 4$*lnBCAA+$\beta 5$*lnKetoneBody; this model may be denoted MMX1. In some embodiments, the system may be further configured to calculate an MMX using the following model: MMX=$\beta 4$*lnBCAA+$\beta 5$*lnKetoneBody+$\beta 6$*lnCitrate+$\beta 7$*lnProtein. In another embodiment, the system may be further configured to calculate the MMX using the following model: MMX=$\beta 4$*lnBCAA+$\beta 5$*lnKetoneBody+$\beta 6$*lnCitrate+$\beta 7$*lnProtein+$\beta 8$*(lnCitrate*lnProtein). In such embodiments, MMX may be described as follows: MMX=$\beta 9$*MMX1+$\beta 10$*MMX2, where MMX1 is as described above, and MMX2=$\beta 6$*lnCitrate+$\beta 7$*lnProtein+$\beta 8$*(lnCitrate*lnProtein).

Additional aspects of the present disclosure are directed to methods of monitoring a patient to evaluate a therapy or determine whether the patient is at-risk of premature mortality. The methods may include: programmatically providing at least one defined MVX mathematical model as disclosed herein that includes a plurality of components including NMR derived measurements of at least one selected HDLP subclass, at least one of a branched chain amino acid, at least one ketone body, and GlycA and optionally at least one of protein or citrate. The method may further comprise programmatically deconvolving a spectrum comprising the NMR derived measurements. The method may also comprise programmatically calculating a MVX score of the respective patients using the at least one defined model and corresponding patient sample measurements; and evaluating at least one of (i) whether the MVX score is above a defined level of a population norm associated with increased risk of all-cause mortality; and/or (ii) whether the metabolic vulnerability index is increasing or decreasing over time in response to a therapy. In some embodiments, the MVX score may be calculated based on the measurements of GlycA, at least one ketone body, at least one branched chain amino acid, and the at least one of the HDLP subclass using the following formula: MVX=A+$\beta 1$*lnGlycA+$\beta 2$*lnS-HDLP+$\beta 4$*lnBCAA+$\beta 5$*lnKetoneBody. In some embodiments, the MVX score may be calculated using the following model: MVX=A+$\beta 1$*lnGlycA+$\beta 2$*lnS-HDLP+$\beta 3$*(lnGlycA*lnS-HDLP)+$\beta 4$*lnBCAA+$\beta 5$*lnKetoneBody. In some embodiments, the MVX score may be calculated using the following model: MVX=A+$\beta 1$*lnGlycA+$\beta 2$*lnS-HDLP+$\beta 3$*(lnGlycA*lnS-HDLP)+$\beta 4$*lnBCAA+$\beta 5$*lnKetoneBody+$\beta 6$*lnCitrate+$\beta 7$*lnProtein+$\beta 8$*(lnCitrate*lnProtein). In some embodiments, the MVX score calculation may comprise an inflammation index (INFX) value and a metabolic malnutrition index (MMX) value. Thus, in some embodiments, the calculation of an MVX score may be based on the following model: MVX=$\beta i$*INFX+$\beta m$*MMX. In these embodiments, the calculation of an INFX value may use the following model: INFX=$\beta 1$*lnGlycA+$\beta 2$*lnS-HDLP+$\beta 3$*(lnGlycA*lnS-HDLP). In some embodiments, the calculation of an MMX value may use the following model: MMX=$\beta 4$*lnBCAA+$\beta 5$*lnKetoneBody; this model may be denoted MMX1. In some embodiments, the calculation of an MMX score may the following model: MMX=$\beta 4$*lnBCAA+$\beta 5$*lnKetoneBody+$\beta 6$*lnCitrate+$\beta 7$*lnProtein. In another embodiment, the calculation of the MMX score may use the following model: MMX=$\beta 4$*lnBCAA+$\beta 5$*lnKetoneBody+$\beta 6$*lnCitrate+$\beta 7$*lnProtein+$\beta 8$*(lnCitrate*lnProtein). In such embodiments, MMX may be described as follows: MMX=$\beta 9$*MMX1+$\beta 10$*MMX2, where MMX1 is as described above, and MMX2=$\beta 6$*lnCitrate+$\beta 7$*lnProtein+$\beta 8$*(lnCitrate*lnProtein).

Further features, advantages, and details of the present disclosure will be appreciated by those of ordinary skill in the art from a reading of the figures and the detailed description of the preferred embodiments that follow, such description being merely illustrative of the present disclosure. Features described with respect with one embodiment can be incorporated with other embodiments although not specifically discussed therewith. That is, it is noted that aspects of the disclosure described with respect to one embodiment, may be incorporated in a different embodiment although not specifically described relative thereto. That is, all embodiments and/or features of any embodiment can be combined in any way and/or combination. The foregoing and other aspects of the present disclosure are explained in detail in the specification set forth below.

As will be appreciated by those of skill in the art in light of the present disclosure, embodiments of the present disclosure may include methods, systems, apparatus and/or computer program products or combinations thereof.

BRIEF DESCRIPTION OF THE FIGURES

FIG. 4 is a table showing the predictive strengths ($\chi^2$) and statistical significance (p value) of parameters, including those used to calculate INFX, MMX, and MVX, in a Cox proportional hazards prediction model for mortality in the CATHGEN study population in accordance with an embodiment of the disclosure. During 5 years of follow-up there were 1259 deaths among 6936 CATHGEN participants.

FIG. 5 displays two tables showing the predictive strengths and statistical significance of parameters in Cox prediction models for mortality during 5-year follow-up in the CATHGEN study. The model on the left includes the inflammation index (INFX) and metabolic malnutrition index (MMX) parameters, and the model on the right includes the MVX parameter, each in accordance with an embodiment of the disclosure.

FIG. 6 displays two tables showing the predictive strengths and statistical significance of parameters, including MVX in accordance with one embodiment of the disclosure, in Cox prediction models for mortality occurring short-term during 1 year of follow-up (left table) and longer-term during a mean of 7 years of follow-up (right table) in the CATHGEN study population.

FIG. 7 is a table showing the predictive strengths, as provided by the likelihood ratio chi-square statistic, of Cox prediction models containing MVX alone (top row) or MVX plus 9 additional covariate parameters (bottom row) for mortality occurring during 3 follow-up periods in the CATHGEN study population in accordance with embodiments of the disclosure.

FIG. 8 Right Panel is a graph that shows cumulative mortality rates over 12 years of follow-up in male participants in the MESA study stratified by quintile of the MVX score according to embodiments of the present disclosure. Among 3198 male MESA participants, 554 died during 12 years of follow-up.

FIG. 9 is a table showing the predictive strengths and statistical significance of MVX determined in accordance with an embodiment of the disclosure and other parameters for non-CVD mortality and the fatal and non-fatal components of the composite CVD outcome, as assessed in a multinomial logistic regression model for participants in MESA.

FIG. 10 is a table showing the predictive strengths and statistical significance of MVX determined in accordance with an embodiment of the disclosure and other parameters for the dual outcomes of congestive heart failure (CHF) and mortality as assessed in a multinomial logistic regression model for participants in MESA.

FIG. 11 is a table showing the predictive strengths and statistical significance of MVX determined in accordance with an embodiment of the disclosure and other parameters for the dual outcomes of cancer and mortality as assessed in a multinomial logistic regression model for participants in MESA.

FIG. 12 is a table showing the predictive strengths and statistical significance of MVX determined in accordance with an embodiment of the disclosure and other parameters for the dual outcomes of chronic kidney disease (CKD) and mortality as assessed in a multinomial logistic regression model for participants in MESA.

FIG. 16 shows an example of analyses used to develop INFX, MMX1, MMX2, MMX scores generally and in different patient populations in accordance with embodiments of the present disclosure.

Figure 1:
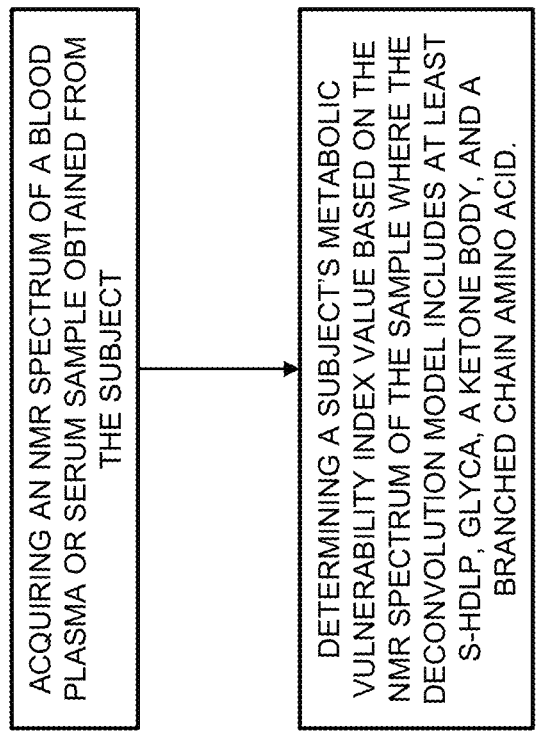
FIG. 1 shows a schematic of a method to measure MVX in accordance with one embodiment of the disclosure.

The foregoing and other objects and aspects of the present disclosure are explained in detail in the specification set forth below.

DETAILED DESCRIPTION

The present disclosure now is described more fully hereinafter with reference to the accompanying drawings, in which embodiments of the disclosure are shown. This disclosure may, however, be embodied in many different forms and should not be construed as limited to the embodiments set forth herein; rather, these embodiments are provided so that this disclosure will be thorough and complete, and will fully convey the scope of the disclosure to those skilled in the art.

Like numbers refer to like elements throughout. In the figures, the thickness of certain lines, layers, components, elements or features may be exaggerated for clarity. Broken lines illustrate optional features or operations unless specified otherwise.

A. Definitions and Terms

The terminology used herein is for the purpose of describing particular embodiments only and is not intended to be limiting of the disclosure. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. As used herein, phrases such as "between X and Y" and "between about X and Y" should be interpreted to include X and Y. As used herein, phrases such as "between about X and Y" mean "between about X and about Y." As used herein, phrases such as "from about X to Y" mean "from about X to about Y."

Unless otherwise defined, all terms (including technical and scientific terms) used herein have the same meaning as commonly understood by one of ordinary skill in the art to which this disclosure belongs. It will be further understood that terms, such as those defined in commonly used dictionaries, should be interpreted as having a meaning that is consistent with their meaning in the context of the specification and relevant art and should not be interpreted in an idealized or overly formal sense unless expressly so defined herein. Well-known functions or constructions may not be described in detail for brevity and/or clarity.

It will be understood that, although the terms first, second, etc. may be used herein to describe various elements, components, regions, layers and/or sections, these elements, components, regions, layers and/or sections should not be limited by these terms. These terms are only used to distinguish one element, component, region, layer or section from another region, layer or section. Thus, a first element, component, region, layer or section discussed below could be termed a second element, component, region, layer or section without departing from the teachings of the present disclosure. The sequence of operations (or steps) is not limited to the order presented in the claims or figures unless specifically indicated otherwise.

The term "programmatically" means carried out using computer program and/or software, processor or ASIC directed operations. The term "electronic" and derivatives thereof refer to automated or semi-automated operations carried out using devices with electrical circuits and/or modules rather than via mental steps and typically refers to operations that are carried out programmatically. The terms "automated" and "automatic" means that the operations can be carried out with minimal or no manual labor or input. The term "semi-automated" refers to allowing operators some input or activation, but the calculations and signal acquisition as well as the calculation of the concentrations of the ionized constituent(s) are done electronically, typically programmatically, without requiring manual input.

The term "about" refers to +/−10% (mean or average) of a specified value or number.

The term "patient" is used broadly and refers to an individual who provides a biosample for testing or analysis.

The term "GlycA" refers to a biomarker that is derived from a measure of composite NMR signal from carbohydrate portions of acute phase reactant glycoproteins containing N-acetylglucosamine and/or N-acetylgalactosamine moieties, more particularly from the protons of the 2-NAcGlc and 2-NAcGal methyl groups. The GlycA signal is centered at about 2.00 ppm in a plasma NMR spectrum at about 47 degrees C. (+/−0.5 degrees C.). The peak location is independent of spectrometer field but may vary depending on analysis temperature of the biosample and is not found in urine biosamples. Thus, the GlycA peak region may vary if the temperature of the test sample varies. The GlycA NMR signal may include a subset of NMR signals at the defined peak region so as to include only clinically relevant signal contributions and may exclude a protein contribution to the signal in this region as will be discussed further below. See U.S. Pat. Nos. 9,361,429, 9,470,771, and 9,792,410, the contents of which are hereby incorporated by reference as if recited in full herein.

As used herein, the chemical shift locations (ppm) refer to NMR spectra referenced internally or externally. In an embodiment, the location may be referenced internally to CaEDTA signal at 2.519 ppm. Thus, the noted peak locations discussed and/or claimed herein may vary depending on how the chemical shift is generated or referenced as is well known to those of skill in the art. Thus, to be clear, certain of the described and/or claimed peak locations have equivalent different peak locations in other corresponding chemical shifts as is well known to those of skill in the art.

The term "biosample" refers to in vitro blood, plasma, serum, CSF, saliva, lavage, sputum, or tissue samples of humans or animals. Embodiments of the disclosure may be particularly suitable for evaluating human blood plasma or serum biosamples, particularly for GlycA (which is not found in urine, for example). The blood plasma or serum samples may be fasting or non-fasting.

The terms "population norm" and "standard" refer to values defined by a large study or studies of average-risk patients such as those enrolled in the Framingham Offspring Study or Multi-Ethnic Study of Atherosclerosis (MESA), or higher-risk patients such as those enrolled in the Catheterization Genetics (CATHGEN) cardiac catheterization biorepository, or other study having a large enough sample to be representative of the general population or targeted patient population. As used herein, the term low-risk (or normal risk) denotes individuals who have not had a known cardiovascular event. Such populations are also known as primary prevention populations. For example, MESA is a low-risk population. As used herein, the term high-risk denotes individuals who have had a known cardiovascular event. Such populations are also known as secondary prevention populations. For example, CATHGEN is a high-risk population. However, the instant disclosure is not limited to the population values in MESA or CATHGEN as the presently defined normal or low-risk and high-risk population values or levels may change over time. Thus, a reference range associated with values from a defined population in risk segments (e.g., quartiles or quintiles) can be provided and used to assess elevated or reduced levels and/or risk of having a clinical disease state.

The term "clinical disease state" is used broadly and includes an at-risk medical condition that may indicate medical intervention, therapy, therapy adjustment or exclusion of a certain therapy (e.g., pharmaceutical drug) and/or monitoring is appropriate. Identification of a likelihood of a clinical disease can allow a clinician to treat, delay or inhibit onset of the condition accordingly.

As used herein, the term "NMR spectral analysis" means using proton ($^1$H) nuclear magnetic resonance spectroscopy techniques to obtain data that can measure the respective parameters present in the biosample, e.g., blood plasma or blood serum. "Measuring" and derivatives thereof refers to determining a level or concentration and/or for certain lipoprotein subclasses, measuring the average particle size thereof. The term "NMR derived" means that the associated measurement is calculated using NMR signal/spectra from one or more scans of an in vitro biosample in an NMR spectrometer.

The term "downfield" refers to a region/location on the NMR spectrum that pertains to the left of a certain peak/location/point (higher ppm scale relative to a reference). Conversely, the term "upfield" refers to a region/location on the NMR spectrum that pertains to the right of a certain peak/location/point.

The terms "mathematical model" and "model" are used interchangeably and when used with "MVX", "metabolic vulnerability index", or "risk", refer to a statistical model of risk used to evaluate a subject's risk of premature mortality in the future, typically within 1-12 years. The risk model can be or include any suitable model including, but not limited to, one or more of a logistic regression model, a Cox proportional hazards regression model, a mixed model, or a hierarchical linear model. The risk models can provide a measure of risk based on the probability of premature mortality within a defined time frame, typically within 1-12 years. The risk models may be particularly suitable for providing risk stratification for patients having "intermediate risk" associated with a slight to moderate chance of having a clinical event based on traditional risk factors. The MVX risk model can stratify a relative risk of premature mortality as measured by standard $\chi^2$ and/or p values (the latter with a sufficiently representative study population).

The term "interaction parameter" refers to at least two different defined parameters combined as a (multiplied) product and/or ratio. Examples of interaction parameters include, but are not limited to, (S-HDLP)(GlycA) and (protein)(citrate).

The term "multimarker" refers to a multi-component biomarker.

The term "lipoprotein component" refers to a component in the mathematical risk model associated with lipoprotein particles including size and/or concentration of one or more subclasses (subtypes) of lipoproteins. Lipoprotein components can include any of the lipoprotein particle subclasses, concentrations, sizes, ratios and/or mathematical products (multiplied) of lipoprotein parameters and/or lipoprotein subclass measurements of defined lipoprotein parameters or combined with other parameters such as GlycA.

The term "HDLP" refers to a high density lipoprotein particle number measurement (e.g., HDLP number) that sums the particle concentrations of defined HDL subclasses. Total HDLP can be generated using a total high density lipoprotein particle measurement that sums the concentration (µmol/L) of all the HDL subclasses (which may be grouped based on size into different size categories such as large, medium and small) in the size range between about 7 nm (on average) to about 14 nm (on average), typically between 7.4-13.5 nm. In some embodiments, HDL can be identified as a number of discrete size components, e.g., 7 subpopulations (H1-H7) of different sizes of HDLP ranging from a smallest HDLP size associated with H1 to a largest HDLP size associated with H7. In some embodiments, the defined subclass of HDL particles comprises small HDL particles (S-HDLP). In some embodiments, the S-HDLP can include HDL particle subclasses with diameters between about 7.3 nm (average) to about 9.0 nm (average).

An "unprocessed biosample" as used herein refers to a biosample that, unlike sample preparation for mass spectrometry analysis, is not subjected to processing that causes the biosample to be physically or chemically altered after it is obtained (but buffers and diluents can be used). Thus, once the biosample is obtained, components from the biosample are not altered or removed. For example, once a blood serum biosample is obtained, the serum is not subjected to processing that removes components from the serum. In some embodiments, an unprocessed biosample is not subjected to filtering and/or ultrafiltration processes.

B. Methods to Determine a Subject's MVX

Herein are disclosed methods and systems to determine a subject's metabolic vulnerability index (MVX). The methods comprise utilizing a multi-variate model of defined biomarkers to predict a patient's chance of premature mortality. Methods include steps of obtaining a sample from a subject and measuring GlycA, at least one high density lipoprotein particle (HDLP) subclass, at least one branched chain amino acid (BCAA), and at least one ketone body; and calculating the subject's metabolic vulnerability index value based on the measurements. In an embodiment, the HDLP is a small HDLP (S-HDLP). In some embodiments, the MVX score may be calculated based on the measurements of GlycA, at least one ketone body, at least one branched chain amino acid, and the at least one of the HDLP subclass using the following formula: $MVX=A+\beta1*lnGlycA+\beta2*lnS\text{-}HDLP+\beta4*lnBCAA+\beta5*lnKetoneBody$. In some embodiments, the MVX score may be calculated using the following model: $MVX=A+\beta1*lnGlycA+\beta2*lnS\text{-}HDLP+\beta3*(lnGlycA*lnS\text{-}HDLP)+\beta4*lnBCAA+\beta5*lnKetoneBody$. In these embodiments, the MVX value may be determined in a subject deemed to be at low risk for a cardiovascular event.

In some embodiments, the MVX value may include a measurement of serum protein (Protein) and/or citrate (Citrate). In some embodiments, the MVX value may be determined using the following model: $MVX=A+\beta1*lnGlycA+\beta2*lnS\text{-}HDLP+\beta3*(lnGlycA*lnS\text{-}HDLP)+\beta4*lnBCAA+\beta5*lnKetoneBody+\beta6*lnCitrate+\beta7*lnProtein+\beta8*(lnCitrate*lnProtein)$. In these embodiments, the MVX value may be determined in a subject deemed to be at high risk for a cardiovascular event.

In an alternative embodiment, the MVX value may comprise an inflammation index (INFX) and/or a metabolic malnutrition index (MMX) as disclosed in more detail herein. Thus, in some embodiments, the calculation of an MVX score may be based on the following model: $MVX=\beta i*INFX+\beta m*MMX$. In these embodiments, the calculation of an INFX value may use the following model: $INFX=\beta1*lnGlycA+\beta2*lnS\text{-}HDLP+\beta3*(lnGlycA*lnS\text{-}HDLP)$. In some embodiments, the calculation of an MMX value may use the following model: $MMX=\beta4*lnBCAA+\beta5*lnKetoneBody$; this model may be denoted MMX1 and be used for subjects deemed to be at low risk for a cardiovascular disease-related event. In some embodiments, the calculation of an MMX score may the following model: $MMX=\beta4*lnBCAA+\beta5*lnKetoneBody+\beta6*lnCitrate+\beta7*lnProtein$. In another embodiment, the calculation of the MMX score may use the following model: $MMX=\beta4*lnBCAA+\beta5*lnKetoneBody+\beta6*lnCitrate+\beta7*lnProtein+\beta8*(lnCitrate*lnProtein)$. In such embodiments, MMX may be described as follows: $MMX=\beta9*MMX1+\beta10*MMX2$, where MMX1 is as described above, and $MMX2=\beta6*lnCitrate+\beta7*lnProtein+\beta8*(lnCitrate*lnProtein)$; in these embodiments, the MVX score may be determined for subjects deemed to be at high risk for a cardiovascular disease-related event.

In some embodiments, the BCAA may be at least one of leucine, isoleucine, or valine. In some embodiments, the ketone bodies may be at least one of acetone, acetoacetate, or beta-hydroxybutyrate. In some embodiments, measuring is performed by NMR.

The metabolic vulnerability index can provide short (1 year) to long (12 year) term premature death risk assessments. These risk assessments can generate MVX values decoupled from traditional risk factors.

FIG. 1 shows a schematic of an embodiment of a method to determine a subject's MVX value. The method may comprise the initial step of acquiring a nuclear magnetic resonance (NMR) spectrum of a blood plasma or serum sample obtained from a subject. Next, calculated lineshapes may be generated for the sample, the lineshapes being based on derived concentrations of lipoprotein and metabolite components potentially present in the sample (the derived concentration of each being the function of a reference spectrum for that component and a calculated reference coefficient). The method may conclude with determining the subject's MVX value based on the NMR spectrum of the sample. This method can enable the practitioner, during a routine and easily-conducted screening, to identify the premature mortality risk in a subject and to begin diagnosis and treatment of conditions associated with premature mortality, or to prevent a subject from receiving medications which may be deleterious.

Figure 2:
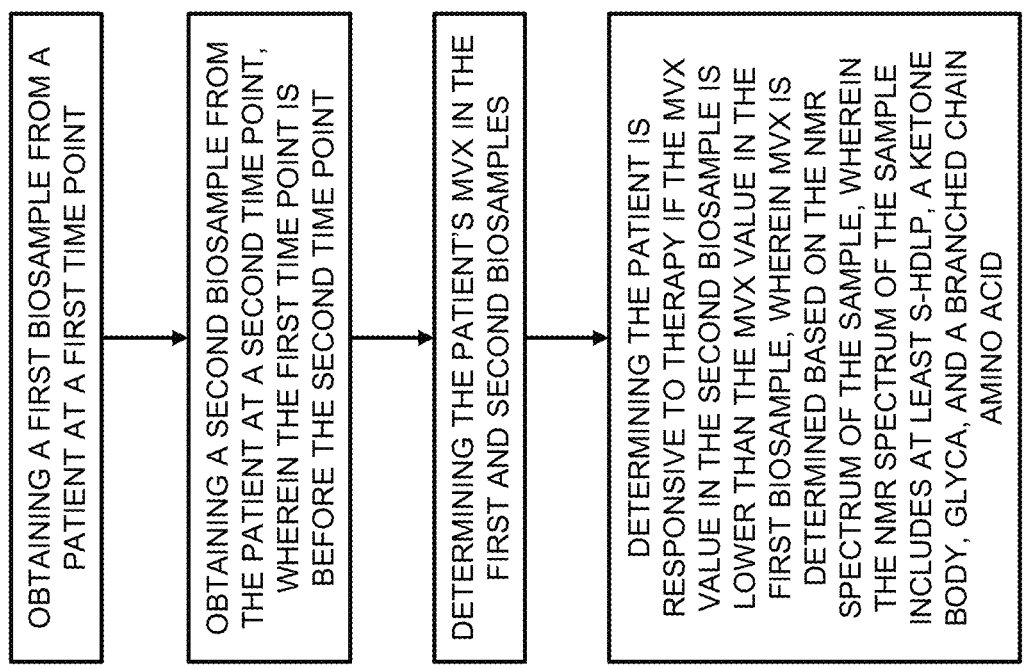
FIG. 2 shows a schematic of a method to use MVX measurements in accordance with one embodiment of the disclosure.

FIG. 2 is a schematic showing an example of how to use MVX to determine a patient's response to therapy. The multi-variate model can be used for assessing patients for entry into or during clinical trials, during a therapy or therapies, for drug development, and/or to identify or monitor anti-inflammatory, anti-obesity, or other drug or nutritional therapy candidates.

In some embodiments, the measurements are obtained by obtaining an NMR signal of an in-vitro blood plasma or serum patient sample to determine NMR derived concentration measurements of the HDL particle subclasses, GlycA, and/or the plurality of metabolic malnutrition biomarkers such as ketone bodies and BCAAs.

Embodiments of the disclosure provide risk assessments of a subject's risk of premature all-cause mortality using a multi-parameter (multi-variate) model of defined predictive biomarkers.

The multi-variate risk assessment model can include at least one defined HDLP component, such as, but not limited to, S-HDLP, at least one ketone body, at least one defined branched chain amino acid, and GlycA. Additionally, the risk assessment model can include one or more of citrate and serum protein.

The multi-variate model can include at least one of the following: NMR measurements of GlycA, branched chain amino acids, citrate, ketone bodies, total protein, and an HDLP component (e.g., subclass) derived from the same NMR spectrum.

The at least one HDLP component of the defined mathematical model of risk may include a first interaction parameter of the measurement of GlycA multiplied by a concentration of a defined HDLP subpopulation. The defined subpopulation of HDL particles can include small HDL particles (S-HDLP). In some embodiments, the S-HDLP can include HDL particle subclasses with diameters between about 7.3 nm (average) to about 9.0 nm (average).

Embodiments of the disclosure provide new biomarkers that can stratify premature mortality risk for patients in both low- and high-risk categories.

Embodiments of the disclosure may be particularly suitable to stratify risk for patients with similar traditional risk factors. Generally stated, it is contemplated that MVX scores can be used to stratify relative risk for premature death. MVX scores can stratify premature death risk for patients having the same age, gender, blood pressure, and BMI independently of these clinical factors.

Embodiments of the disclosure can evaluate a patient's risk of premature mortality within a 1-12 year time frame using a plurality of risk model parameters.

As noted above, embodiments of the disclosure can include biomarkers that link to inflammation (e.g., INFX) and metabolic malnutrition (e.g., MMX), as shown in Table 1. In some embodiments, the MVX score may be defined as comprising an inflammation index (INFX) value and a metabolic malnutrition index (MMX) value. In some embodiments of the disclosure, a method of determining the levels of markers associated with a subject's relative risk of premature death may comprise obtaining a sample from the subject; measuring GlycA, at least one high density lipoprotein particle (HDLP) subclass, at least one branched chain amino acid (BCAA), and at least one ketone body (KetoneBody) and optionally at least one of citrate (Citrate) and serum protein (Protein); using the measurement of GlycA and the at least one HDLP subclass to generate an inflammation index (INFX) value; using the measurement of the at least one BCAA and the at least one ketone body, and optionally, the Protein and Citrate, to generate at least one metabolic malnutrition index (MMX) value; and determining a metabolic vulnerability index (MVX) value based on the INFX and MMX values.

TABLE 1

| PATHOPHYSIOLOGY/BIOMARKERS | |
|---|---|
| Pathophysiology | BioMarker(s) |
| Inflammation | GlycA, HDL |
| Metabolic Malnutrition | Serum Protein, Ketone Bodies, Citrate, BCAAs |

Inflammation can be associated with many different disease states including, but not limited to, CVD. It is also believed that inflammation may modulate HDL functionality. See, e.g., Fogelman, *When Good Cholesterol Goes Bad*, Nature Medicine, 2004. Carbohydrate components of glycoproteins can perform biological functions in protein sorting, immune and receptor recognition, inflammation and other cellular processes.

As disclosed herein, the MVX model(s) can include at least two inflammatory markers, such as GlycA and S-HDLP and at least two metabolic malnutrition biomarkers, such as at least one ketone body and at least one BCAA. In some embodiments, the MVX models include at least one interaction parameter.

The MVX mathematical models can consider other clinical parameters such as gender, age, BMI, whether on hypertension medicine and the like, or the MVX mathematical models can generate a MVX value independently of any clinical parameters.

As noted above, embodiments of the present disclosure may be used to generate at least one MVX score using one or more defined mathematical models of risk. The model(s) may utilize measurements of different defined biomarkers or parameters from an in vitro biosample of a patient at risk of premature mortality who may benefit from pharmaceutical, medical, nutritional, exercise, or other intervention.

The MVX evaluation can be decoupled from a traditional Framingham or other risk evaluation and can be relatively easily used as a screening tool and may be able to identify at-risk individuals earlier in time than with conventional tests.

Figure 3:
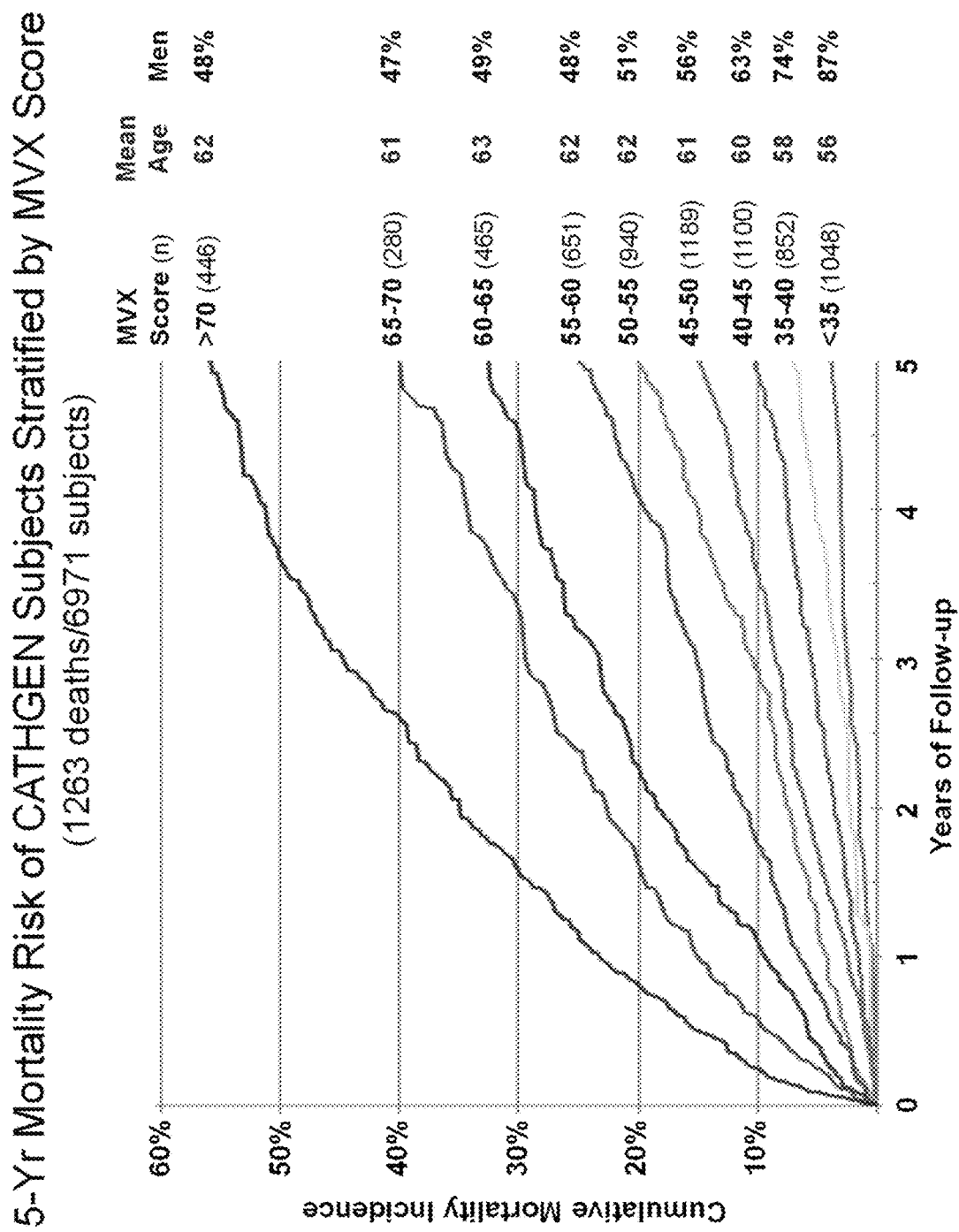
FIG. 3 is a graph that shows cumulative mortality rates over 5 years for subgroups of CATHGEN participants stratified by MVX score according to embodiments of the present disclosure. In total, 1263 participants died during 5 years of follow-up.

For example, FIG. 3 is a graph that shows the cumulative mortality rates over five years for 9 subgroups of high-risk cardiac catheterization patients enrolled in CATHGEN stratified by MVX score according to embodiments of the present disclosure. In total, 1263 out of 6971 participants died during five years of follow-up. As shown in FIG. 3, the higher the MVX score, the higher the risk was of dying prematurely. For example, individuals with a high MVX score >70 (red line) had a rate of premature death more than 10 times greater than those with a low MVX score <35 (dark green line). As shown by the mean ages and gender composition of each of the 9 subgroups in FIG. 3, the large differences in mortality rates linked to MVX score are largely independent of age and gender.

In some embodiments, it is contemplated that MVX can be used to stratify mortality risk in high risk populations, such as those in the CATHGEN study, as seen in FIG. 3.

As disclosed herein, MVX values are calculated using multiple parameters including at least measurements of GlycA, S-HDLP, at least one branched chain amino acid, and at least one ketone body. Parameters can also include measurements of citrate and protein and various interaction parameters. FIG. 4 is a table showing the predictive strengths ($\chi^2$) and statistical significance (p value) of traditional risk factors and MVX-related parameters in a Cox proportional hazards prediction model for mortality in the CATHGEN study population. In this table, "BCAA" is the sum of the concentrations of 3 branched-chain amino acids (valine, leucine, isoleucine) and "Ketone Bodies" is the sum of the concentrations of 3 ketone bodies (β-hydroxybutyrate, acetoacetate, acetone). The 6 MVX parameters shown in FIG. 4 (including interaction parameters for lnGlycA*lnS-HDLP and lnCitrate*lnProtein) were used to calculate the MVX scores used for mortality risk stratification in FIG. 3, using the general formula MVX=A+β1*lnGlycA+β2*lnS-HDLP+β3*(lnGlycA*lnS-HDLP)+β4*lnBCAA+β5*lnKetoneBody+β6*lnCitrate+β7*lnProtein+β8*(lnCitrate*lnProtein). MVX values can also be broken down into two component parts: the presumed inflammatory part given by an inflammatory index (INFX) parameter and the presumed malnutrition part given by a metabolic malnutrition index (MMX) parameter. FIG. 5 displays two tables showing the predictive strengths and statistical significance of these parameters as well as MVX in Cox prediction models for mortality during a five year follow-up period in the CATHGEN study. The model on the left includes the INFX and MMX parameters, and the model on the right includes the MVX parameter.

In some embodiments, MVX can be used to predict short and long term premature all-cause mortality risk. FIG. 6 displays two tables showing the predictive strengths and statistical significance of parameters, including MVX, in Cox prediction models for mortality occurring short-term during one year follow-up (left table) and longer-term during a mean of seven years of follow-up (right table) in the CATHGEN study population.

In some embodiments, MVX is calculated independently of traditional risk evaluation parameters. FIG. 7 is a table showing the predictive strengths, as provided by the likelihood ratio chi-square statistic, of Cox prediction models containing MVX alone (top row) or MVX plus 9 additional covariate parameters (age, race, gender, smoking, hypertension, diabetes, BMI, triglyceride-rich lipoprotein particles, and low density lipoprotein particles) for mortality occurring during three follow-up periods in the CATHGEN study population.

Figure 8:
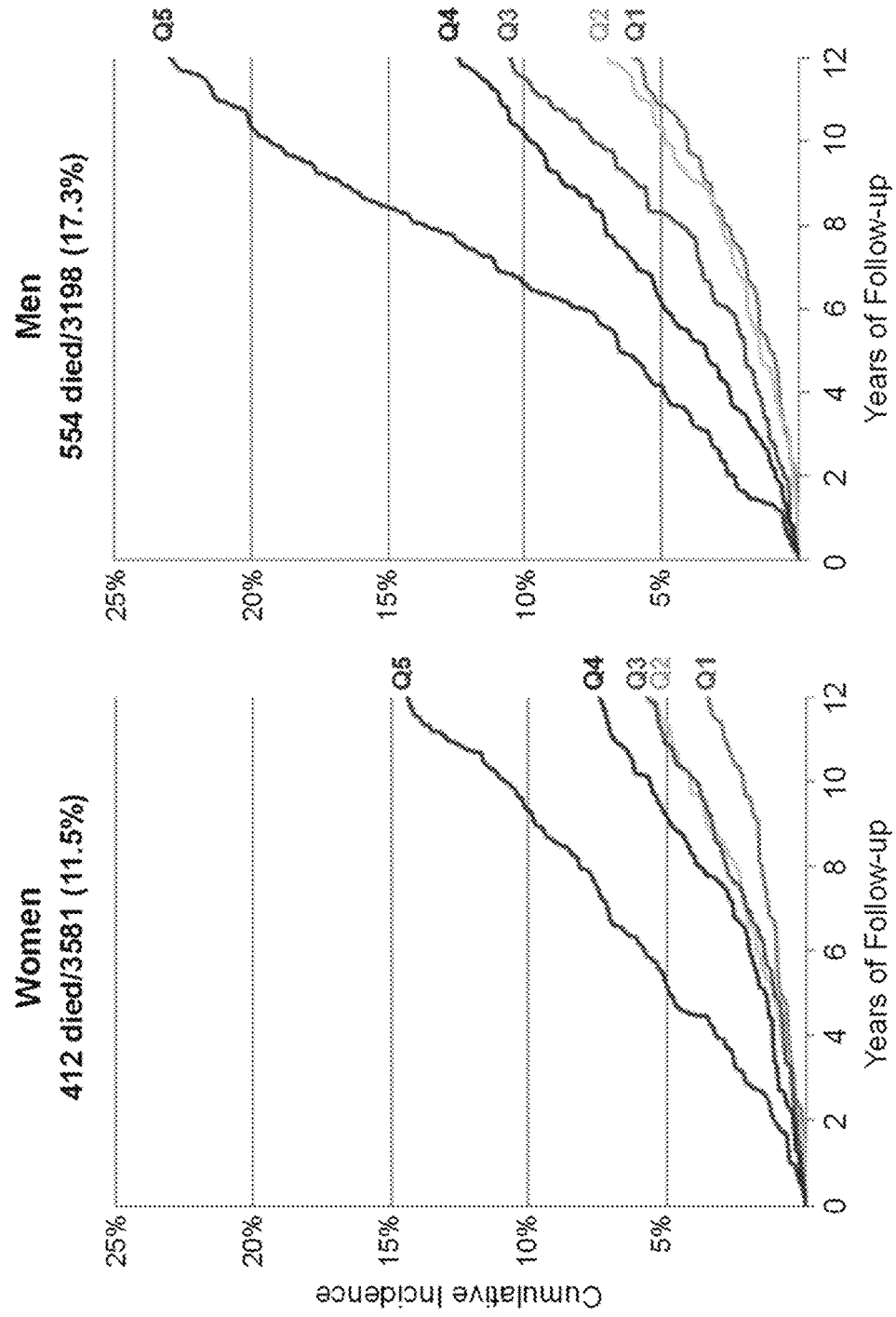
FIG. 8 Left Panel is a graph that shows cumulative mortality rates over 12 years of follow-up in female participants in the MESA study stratified by quintile of the MVX score according to embodiments of the present disclosure. Among 3581 female MESA participants, 412 died during 12 years of follow-up.

In some embodiments, it is contemplated that MVX can be used to stratify mortality risk among low risk populations, as seen in FIG. 8. FIG. 8 Left Panel is a graph that shows cumulative mortality rates over twelve years of follow-up in female participants in the MESA study stratified by quintile of the low risk MVX score (e.g., MVX1) according to embodiments of the present disclosure. Among 3581 female MESA participants, 412 died during 12 years of follow-up. FIG. 8 Right Panel is a graph that shows cumulative mortality rates over 12 years of follow-up in male participants in the MESA study stratified by quintile of the MVX1 score according to embodiments of the present disclosure. Among 3198 male MESA participants, 554 died during 12 years of follow-up.

In some embodiments, it is contemplated that MVX can be used to predict the relative risk of premature mortality irrespective of the disease state(s) considered to be the "cause" of death. FIG. 9 is a table showing the predictive strengths and statistical significance of MVX (e.g., MVX1) and other parameters for four different CVD and mortality outcomes as assessed in a multinomial logistic regression model for participants in MESA (low risk). Three of the four outcomes comprise what is commonly referred to as the composite outcome of "CVD": left column: nonfatal CVD event without death occurring during follow-up (n=432); second column from left: nonfatal CVD event with death occurring later during follow-up (n=128); third column from left: fatal CVD event (n=225). The outcome assessed in the right column is mortality occurring without earlier or concurrent CVD (n=610). The results indicate that MVX is highly predictive (p<0.0001) of the three outcomes that include death, but is not predictive of CVD when not accompanied or followed later by death (p=0.50). Thus, prediction of the fatal and nonfatal component parts of the composite CVD outcome by MVX differs substantially, suggesting the etiology of nonfatal and fatal CVD may be more dissimilar than believed and calling into question the rationale of combining fatal and nonfatal CVD into a single outcome.

Mortality considered to be caused or contributed to by other diseases besides CVD is also predicted by MVX, as shown by the results in FIGS. 10-12. FIG. 10 is a table showing the predictive strengths and statistical significance of MVX (e.g., MVX1) and other parameters for the combined outcomes of congestive heart failure (CHF) and mortality as assessed in a multinomial logistic regression model for participants in MESA (low risk). FIG. 11 is a table showing the predictive strengths and statistical significance of MVX and other parameters for the combined outcomes of cancer and mortality as assessed in a multinomial logistic regression model for participants in MESA. FIG. 12 is a table showing the predictive strengths and statistical significance of MVX and other parameters for the combined outcomes of chronic kidney disease (CKD) and mortality as assessed in a multinomial logistic regression model for participants in MESA.

In some embodiments, gender may be included as a factor in the MVX model. In some embodiments, age may be included as a factor in the MVX model. In other embodiments, the MVX model can exclude either gender or age considerations so as to avoid generating false negatives or false positives based on data corruption of such ancillary data not directly tied to a biosample, for example.

In some embodiments, the MVX score is provided to the clinician based on data electronically correlated to the sample or based on clinician or intake lab input, e.g., fasting "F" or non-fasting "NF," and statin "S" or non-statin "NS" characterizations of the patient which data can be provided on labels associated with the biosample to be electronically associated with the sample at the NMR analyzer. Alternatively, the patient characterization data can be held in a computer database (remote or via server or other defined pathway) and can include a patient identifier, sample type, test type, and the like entered into an electronic correlation file by a clinician or intake laboratory that can be accessed by or hosted by the intake laboratory that communicates with the NMR analyzer. The patient characterization data can allow the appropriate MVX model to be used for a particular patient.

It is contemplated that a metabolic vulnerability index can be used to monitor subjects in clinical trials and/or on drug therapies, to identify drug contradictions, and/or to monitor for changes in risk status (positive or negative) that may be associated with a particular drug, a patient's lifestyle and the like, which may be patient-specific.

Lipoproteins

Lipoproteins include a wide variety of particles found in plasma, serum, whole blood, and lymph, comprising various types and quantities of triglycerides, cholesterol, phospholipids, sphingolipids, and proteins. These various particles permit the solubilization of otherwise hydrophobic lipid molecules in blood and serve a variety of functions related to lipolysis, lipogenesis, and lipid transport between the gut, liver, muscle tissue and adipose tissue. In blood and/or plasma, lipoproteins have been classified in many ways, generally based on physical properties such as density or electrophoretic mobility or measures of apolipoprotein content, such as apoB or apoA-1, the main proteins in LDL and HDL, respectively.

Classification based on nuclear magnetic resonance-determined particle size distinguishes distinct lipoprotein particles based on size or size ranges. For example, the NMR measurements can identify at least 15 distinct lipoprotein particle subtypes, including at least 7 subtypes of high density lipoproteins (HDL), at least 3 subtypes of low density lipoproteins (LDL), and at least 5 subtypes of very low density lipoproteins (VLDL), which can also be designated TRL (triglyceride rich lipoprotein).

Current analysis methodology allows NMR measurements that can provide concentrations of subpopulations of VLDL, LDL, and HDL to produce measurements of groups of small and large subpopulations of respective groups. For example, to optimize risk association with premature all-cause mortality, different size groupings of HDL subpopulations can be used as will be discussed further below.

The NMR derived estimated lipoprotein sizes noted herein typically refer to average measurements, but other size demarcations may be used.

In preferred embodiments, the MVX risk assessment model parameters can include NMR derived measurements of deconvolved signal associated with a common NMR spectrum of lipoproteins, and particularly HDLs, using defined deconvolution models that characterize deconvolution components for protein and lipoproteins, including HDL, LDL, VLDL/TRL. This type of analysis can provide for a rapid acquisition time of under 2 minutes, typically between about 20 s-90 s, and corresponding rapid programmatic calculations to generate measurements of the model components, then programmatic calculation of one or more MVX risk scores using one or more defined risk models.

Further, it is also noted that while NMR measurements of the lipoprotein particles are contemplated as being particularly suitable for the analyses described herein, it is contemplated that other technologies may be used to measure these parameters now or in the future and embodiments of the disclosure are not limited to this measurement methodology. It is also contemplated that different protocols using NMR may be used (e.g., including different deconvolving protocols) in lieu of the deconvolving protocol described herein. See, e.g., Kaess et al., The lipoprotein subfraction profile: heritability and identification of quantitative trait loci, J Lipid Res. Vol. 49 pp. 715-723 (2008); and Suna et al., 1H NMR metabolomics of plasma lipoprotein subclasses: elucidation of metabolic clustering by self-organising maps, NMR Biomed. 2007; 20: 658-672. Flotation and ultracentrifugation employing a density-based separation technique for evaluating lipoprotein particles and ion mobility analysis are alternative technologies for measuring lipoprotein subclass particle concentrations.

Lipoprotein subclass groupings can, for example, be summed to determine HDL or LDL particle numbers according to some particular embodiments of the present disclosure. It is noted that the "small, large, and medium" size ranges noted can vary or be redefined to widen or narrow the upper or lower end values thereof or even to exclude certain ranges within the noted ranges. The particle sizes noted above typically refer to average measurements, but other demarcations may be used.

Embodiments of the disclosure classify lipoprotein particles into subclasses grouped by size ranges based on functional/metabolic relatedness as assessed by their correlations with lipid and metabolic variables. Thus, as noted above, the evaluations can measure over 15 discrete subpopulations (sizes) of lipoprotein particles. These discrete subpopulations can be grouped into defined subclasses for VLDL/TRL and HDL and LDL. Intermediate-density lipoprotein (IDL) can be combined with VLDL/TRL or LDL or as a separate category in the size range between large LDL and small VLDL.

For example, HDL subclass particles typically range (on average) from between about 7 nm to about 15 nm, more typically about 7.3 nm to about 14 nm (e.g., 7.4 nm-13.5 nm). Total HDL concentration is the sum of the particle concentrations of the respective subpopulations of its HDL subclasses. The different subpopulations of HDLP can be identified by a number from 1-7, with "H1" representing the smallest-size HDL subpopulation and "H7" being the largest-size HDL subpopulation. In some embodiments, the defined subclass of HDL particles comprises small HDL particles (S-HDLP). In some embodiments, the S-HDLP can include HDL particle subclasses with diameters between about 7.3 nm (average) to about 9.0 nm (average).

BCAAs

In some embodiments, the MVX model includes the measurement of at least one BCAA, as described in U.S. Pat. No. 9,361,429 and U.S. Pat. App. 20150149095, incorporated by reference herein.

The MVX models may include one or more BCAAs including one or more of isoleucine, leucine, and valine (as discussed herein). In some embodiments, one or more of the set of three BCAAs (valine, leucine, and isoleucine) can be quantified by NMR.

Ketone Bodies

In some embodiments, the MVX model includes the measurement of at least one ketone body (β-hydroxybutyrate, acetoacetate, acetone), which can be obtained via NMR analysis of the biosample NMR spectrum. NMR quantification of each of the 3 ketone bodies is based on their NMR signal amplitudes as derived from separate deconvolution models specific to the 3 spectral regions in which the ketone body NMR signals appear. Deconvolution analysis, rather than simple integration of the ketone body signals, is required because of extensive overlap with signals from numerous lipoprotein subspecies and identified and unidentified small molecule metabolites. The derived amplitudes of the β-hydroxybutyrate, acetoacetate, and acetone signals can be converted to μmol/L units of concentration using conversion factors determined by spiking serum with stock ketone body solutions of known concentration.

In one embodiment, the β-hydroxybutyrate methyl signal doublet appearing at approximately 1.16 and 1.15 ppm is quantified using a lineshape deconvolution model that encompasses the spectral region from 1.07 to 1.33 ppm. This region includes the overlapped interfering NMR signals from lipid fatty acid methylene protons of numerous TRL, LDL, and HDL lipoprotein subspecies, serum protein signals, the triplet signal from ethanol (at 1.13, 1.15, and 1.17 ppm), the doublet signal from lactate (at 1.29 and 1.31 ppm), and a doublet signal from an unidentified metabolite (at 1.10 and 1.11 ppm) that appears only rarely in human serum specimens. In one embodiment, the deconvolution model includes a library of 83 spectral components to accurately account for the amplitudes of the NMR signals from (3-hydroxybutyrate and the various interfering substances in serum.

In one embodiment, the acetoacetate methyl signal singlet appearing at approximately 2.24 ppm is quantified using a lineshape deconvolution model that encompasses the spectral region from 2.22 to 2.39 ppm. This region includes the overlapped interfering NMR signals from lipid fatty acid methylene protons of numerous TRL, LDL, and HDL lipoprotein subspecies, serum protein signals, the octet signals from β-hydroxybutyrate (2.25 to 2.39 ppm), and signals from 3 unidentified metabolites appearing at 2.22, 2.30, and 2.35-2.41 ppm. In one embodiment, the deconvolution model includes a library of 82 spectral components to accurately account for the amplitudes of the NMR signals from acetoacetate and the various interfering substances in serum.

In one embodiment, the acetone methyl signal singlet appearing at 2.19 ppm is quantified using a lineshape deconvolution model that encompasses the spectral region from 2.14 to 2.22 ppm. This region includes the overlapped interfering NMR signals from lipid fatty acid methylene protons of numerous TRL, LDL, and HDL lipoprotein subspecies, serum protein signals, and a singlet signal from an unidentified metabolite at 2.22 ppm. In one embodiment, the deconvolution model includes a library of 70 spectral components to accurately account for the amplitudes of the NMR signals from acetone and the various interfering substances in serum.

GlycA

A defined lineshape GlycA mathematical deconvolution model can be used to measure the GlycA as described in U.S. Pat. No. 9,470,771 incorporated by reference in its entirety herein. The GlycA measurement can be a unitless parameter as assessed by NMR by calculating an area under a peak region at a defined peak location in NMR spectra. In any event, measures of GlycA with respect to a known population (such as MESA) can be used to define the level or risk for certain subgroups, e.g., those having values within the upper half of a defined range, including values in the third and fourth quartiles, or the upper 3-5 quintiles and the like.

Citrate

In some embodiments, the MVX model includes the measurement of citrate, which can be obtained via NMR analysis of the biosample NMR spectrum. NMR quantification of citrate is based on the NMR signal amplitudes of three of the four members of the methylene proton quartet appearing at approximately 2.64, 2.60, and 2.48 ppm as derived from a deconvolution model that assumes a linear baseline and variable offset. The fourth member of the citrate signal quartet appears at approximately 2.52 ppm and overlaps the singlet signal from CaEDTA that serves as an internal chemical shift reference. The derived amplitudes of the citrate signals can be converted to mol/L units of concentration using conversion factors determined by spiking serum with stock citrate solutions of known concentration.

Serum Protein

In some embodiments, the MVX model includes the measurement of serum protein, which can be obtained via NMR analysis of the biosample NMR spectrum. Alternatively, serum protein or serum albumin measurements, where used, can be obtained in conventional ways. NMR quantification of serum protein is based on the amplitude of the broad NMR signal from non-lipoprotein proteins derived from a lineshape deconvolution model that encompasses the spectral region from 0.71 to 1.03 ppm. This region includes the overlapped interfering NMR signals from lipid fatty acid methyl protons of numerous TRL, LDL, and HDL lipoprotein subspecies as well as those from the branched-chain amino acids valine, leucine, and isoleucine. In one embodiment, the deconvolution model includes a library of 66 spectral components to accurately account for the amplitudes of the NMR signals from serum protein and the various interfering substances in serum. The derived amplitude of the serum protein signal can be reported in arbitrary units of signal amplitude or converted to molar units of concentration using conversion factors determined by spiking serum with stock serum albumin solutions of known concentration.

C. Systems to Measure MVX

Referring Some embodiments of the disclosure comprise a system capable of performing each method described herein. In some embodiments, the system may comprise an NMR spectrometer configured to acquire an NMR spectrum and/or spectra comprising at least one signal for GlycA, at least one signal for at least one high density lipoprotein particle (HDLP) subclass, at least one signal for at least one branched chain amino acid (BCAA), and at least one signal for at least one ketone body (KetoneBody); and a processor to determine a metabolic vulnerability index (MVX) value based on the measured at least one signal for the GlycA, the at least one high density lipoprotein particle (HDLP) subclass, the at least one branched chain amino acid (BCAA), and the at least one ketone body (KetoneBody) wherein the processor comprises or communicates with a memory. The system may further comprise an NMR spectrometer configured to acquire an NMR spectrum and/or spectra comprising at least one signal for serum protein (Protein) and/or citrate (Citrate); and a processor to determine a metabolic vulnerability index (MVX) value based on the measured at least one signal for the serum protein (Protein) and the citrate (Citrate).

Referring Some embodiments of the disclosure comprise an NMR system capable of performing each method described herein. In some embodiments, the NMR system may comprise an NMR spectrometer; a flow probe in communication with the spectrometer; and a processor in communication with the spectrometer configured to obtain (i) at least one NMR signal of a defined GlycA fitting region of NMR spectra associated with GlycA of a blood plasma or serum specimen in the flow probe; (ii) at least one NMR signal of a defined ketone body fitting region of NMR spectra associated with the specimen in the flow probe; (iii) at least one NMR signal of a defined BCAA fitting region of NMR spectra associated with the specimen in the flow probe; and, (iv) at least one NMR signal for at least one HDLP subclass; and optionally, at least one NMR signal for serum protein (Protein) and/or citrate (Citrate). In some embodiments, the processor is further configured to calculate an MVX score based on measurements obtained by the spectrometer according to any of the embodiments of the invention disclosed herein.

The flowcharts and block diagrams of certain of the figures herein illustrate the architecture, functionality, and operation of possible implementations of analysis models and evaluation systems and/or programs according to the present invention. In this regard, each block in the flow charts or block diagrams represents a module, segment, operation, or portion of code, which comprises one or more executable instructions for implementing the specified logical function(s). It should also be noted that in some alternative implementations, the functions noted in the blocks might occur out of the order noted in the figures. For example, two blocks shown in succession may in fact be executed substantially concurrently or the blocks may sometimes be executed in the reverse order, depending upon the functionality involved.

Figure 13:
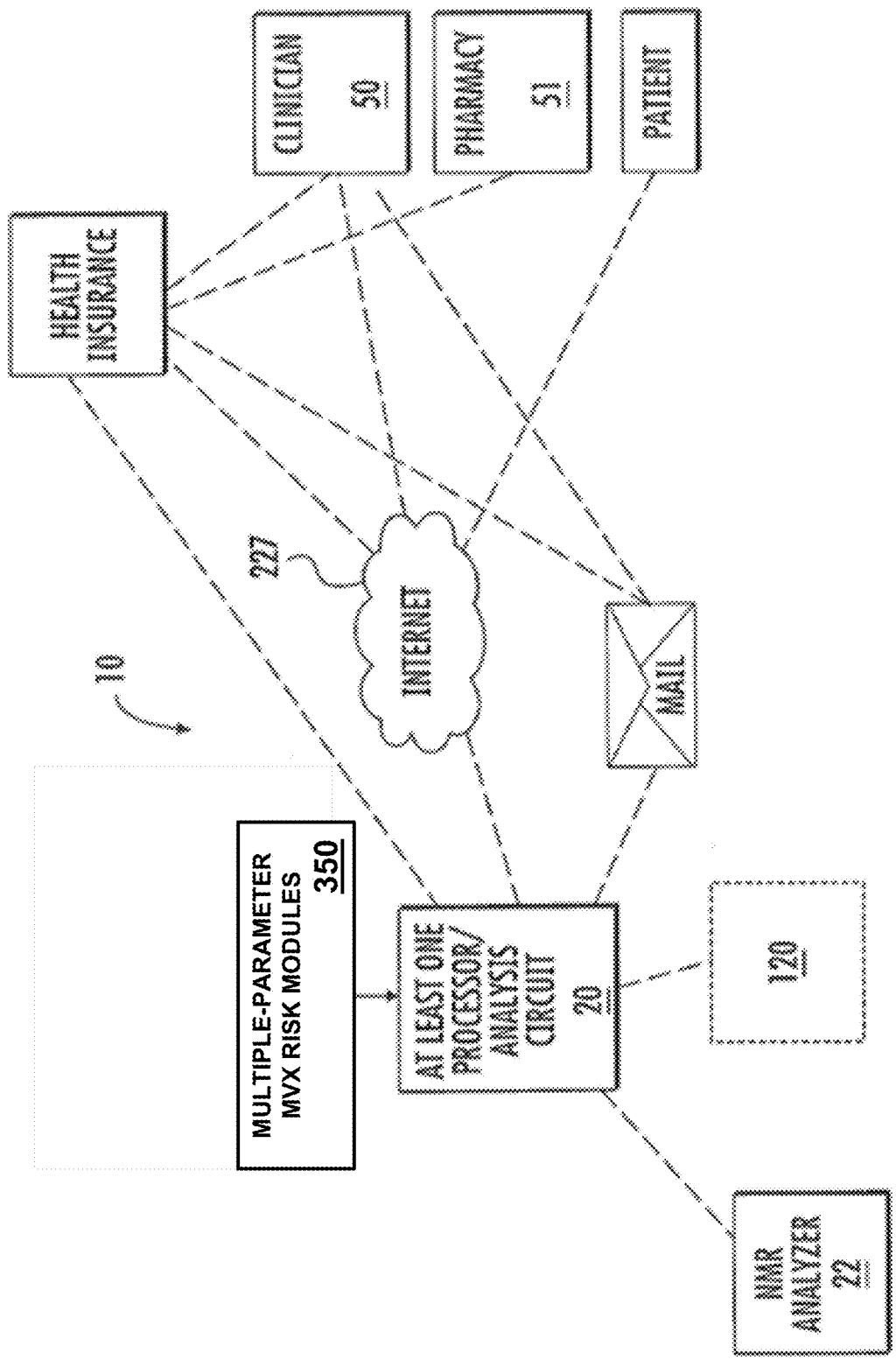
FIG. 13 shows a schematic illustration of a system for MVX evaluation modules and/or circuits according to embodiments of the present disclosure.

Referring now to FIG. 13, it is contemplated that most, if not all, the measurements can be carried out on or using a system 10 in communication with or at least partially onboard an NMR clinical analyzer 22 as described, for example, with respect to U.S. Pat. No. 8,013,602, the contents of which are hereby incorporated by reference as if recited in full herein. The analyzer 22 includes a spectrometer and a sample handler system The system 10 can include a processor (e.g., Metabolic Vulnerability Index Module) 350 to collect data suitable for determining the MVX value that may comprise e.g., GlycA, BCAAs, ketone bodies, HDLP subpopulations such as, but not limited to, S-HDLP, and/or citrate, and/or protein). In some embodiments, the processor may be configured to calculate an MVX score based on the measurements of GlycA, at least one ketone body, at least one branched chain amino acid, and the at least one of the HDLP subclass using the following formula: MVX=A+$\beta1$*lnGlycA+$\beta2$*lnS-HDLP+$\beta4$*lnBCAA+$\beta5$*lnKetoneBody. In some embodiments, the processor may be configured to calculate the MVX score using the following model: MVX=A+$\beta1$*lnGlycA+$\beta2$*lnS-HDLP+$\beta3$*(lnGlycA*lnS-HDLP)+$\beta4$*lnBCAA+$\beta5$*lnKetoneBody. In some embodiments, the processor may be configured to calculate an MVX score using the following model: MVX=A+$\beta1$*lnGlycA+$\beta2$*lnS-HDLP+$\beta3$*(lnGlycA*lnS-HDLP)+$\beta4$*lnBCAA+$\beta5$*ln KetoneBody+$\beta6$*lnCitrate+$\beta7$*lnProtein+$\beta8$*(lnCitrate* lnProtein). In some embodiments, the processor may be configured to calculate an MVX score comprising an inflammation index (INFX) value and a metabolic malnutrition index (MMX) value. Thus, in some embodiments, the processor may be configured to calculate an MVX score based on the following model: MVX=$\beta i$*INFX+$\beta m$*MMX. In these embodiments, the processor may be configured to calculate an INFX value using the following model: INFX=$\beta1$*lnGlycA+$\beta2$*lnS-HDLP+$\beta3$*(lnGlycA*lnS-HDLP). In some embodiments, the processor may be configured to calculate an MMX value using the following model: MMX=$\beta4$*lnBCAA+$\beta5$*lnKetoneBody; this model may be denoted MMX1. In some embodiments, the processor may be configured to calculate an MMX using the following model: MMX=$\beta4$*lnBCAA+$\beta5$*lnKetoneBody+$\beta6$*lnCitrate+$\beta7$*lnProtein. In another embodiment, the processor may be configured to calculate the MMX using the following model: MMX=$\beta4$*lnBCAA+$\beta5$*lnKetoneBody+$\beta6$*lnCitrate+$\beta7$*lnProtein+38*(lnCitrate*lnProtein). In such embodiments, MMX may be described as follows: MMX= $\beta9$*MMX1+$\beta10$*MMX2, where MMX1 is as described above, and MMX2=$\beta6$*lnCitrate+$\beta7$*lnProtein+$\beta8$*(lnCitrate* lnProtein).

The system can include an analysis circuit 20 that includes at least one processor that can be onboard the analyzer 22 or at least partially remote from the analyzer 22. If the latter, the processor/analysis circuit 20 can reside totally or partially on a server. The server can be provided using cloud computing which includes the provision of computational resources on demand via a computer network. The resources can be embodied as various infrastructure services (e.g. computer, storage, etc.) as well as applications, databases, file services, email, etc. In the traditional model of computing, both data and software are typically fully contained on the user's computer; in cloud computing, the user's computer may contain little software or data (perhaps an operating system and/or web browser), and may serve as little more than a display terminal for processes occurring on a network of external computers. A cloud computing service (or an aggregation of multiple cloud resources) may be generally referred to as the "Cloud". Cloud storage may include a model of networked computer data storage where data is stored on multiple virtual servers, rather than being hosted on one or more dedicated servers. Data transfer can be encrypted and can be done via the Internet using any appropriate firewalls to comply with industry or regulatory standards such as HIPAA. The term "HIPAA" refers to the United States laws defined by the Health Insurance Portability and Accountability Act. The patient data can include an accession number or identifier, gender, age and test data.

The results of the MVX determination can be transmitted via a computer network, such as the Internet 227, via email or the like to a patient, clinician site 50, to a health insurance agency or a pharmacy 51. The results can be sent directly from the analysis site or may be sent indirectly. The results may be printed out and sent via conventional mail. This information can also be transmitted to pharmacies and/or medical insurance companies, or even patients that monitor for prescriptions or drug use that may result in an increased risk of an adverse event or to place a medical alert to prevent prescription of a contradicted pharmaceutical agent. The results can be sent to a patient via email to a "home" computer or to a pervasive computing device such as a smart phone or notepad and the like. The results can be as an email attachment of the overall report or as a text message alert, for example.

One or more electronic devices associated with the different users, e.g., a clinician site, patient and/or a test or lab site can be configured to access an electronic analysis circuit in communication with a display of a respective electronic device. The analysis circuit can be hosted on a server and can provide an internet portal or downloadable APP or other computer program for various devices. The circuit can configured to allow a user, e.g., a clinician to enter one or more of: (i) a traditional risk factor value of a patient, (ii) a traditional risk factor value of a patient and a personal vulnerability index score, or (iii) a personal vulnerability index score. The circuit can automatically populate different data fields based on a patient identifier or other password at sign-in or allow a user to enter both the MVX score and the traditional factor measurement for a respective patient. The analysis circuit can be configured to track changes in the MVX score over time and generate electronic reports that can be sent to clinicians, patients or other users. The analysis circuit can also send notices for recommendations on retests, follow-up tests and the like, e.g., if a MVX risk score is elevated or above a low risk value, e.g., in an intermediate risk category, the circuit can notify the clinician that further testing may be appropriate or send a notice to the patient to confer with the doctor to see what test is appropriate or whether increased monitoring intervals for follow-up MVX tests may be desirable. The analysis circuit can generate a risk assessment pathway or analysis to provide graphic information that stratifies risk of premature all-cause mortality in the future for patients having the same traditional risk factor values. The electronic analysis circuit can be onboard the server in the Cloud or otherwise accessible via the Internet or can be associated with a different client architecture as will be appreciated by one of skill in the art. Thus, a clinician, patient or other user can generate a customized report on risk assessment or otherwise obtain risk stratification information.

Figure 14:
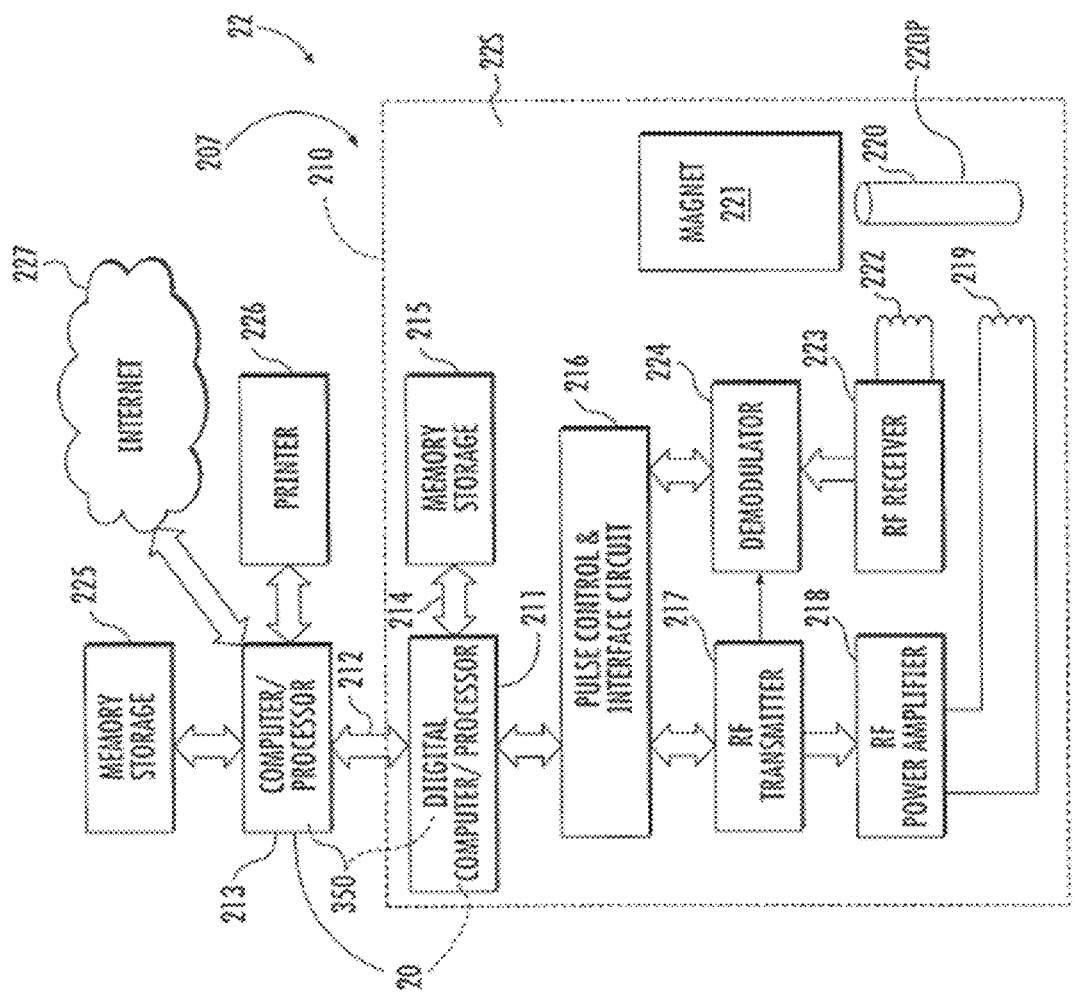
FIG. 14 shows a schematic illustration of a NMR spectroscopy apparatus according to embodiments of the present disclosure.

FIG. 14 shows an example of the measurement of MVX using NMR. Some embodiments of the disclosure comprise an NMR system capable of performing each method described herein. In some embodiments, the NMR system may comprise an NMR spectrometer; a flow probe in communication with the spectrometer; and a processor in communication with the spectrometer configured to obtain (i) at least one NMR signal of a defined GlycA fitting region of NMR spectra associated with GlycA of a blood plasma or serum specimen in the flow probe; (ii) at least one NMR signal of a defined ketone body fitting region of NMR spectra associated with the specimen in the flow probe; (iii) at least one NMR signal of a defined BCAA fitting region of NMR spectra associated with the specimen in the flow probe; and, (iv) at least one NMR signal for at least one HDLP subclass; and optionally, at least one NMR signal for serum protein (Protein) and/or citrate (Citrate). In some embodiments, the processor is further configured to calculate an MVX score based on measurements obtained by the spectrometer according to any of the embodiments of the invention disclosed herein.

Referring now to FIG. 14, a system 207 for acquiring and calculating the lineshape of a selected sample is illustrated. The system 207 includes an NMR spectrometer 22 for taking NMR measurements of a sample. In one embodiment, the spectrometer 22 is configured so that the NMR measurements are conducted at 400 MHz for proton signals; in other embodiments the measurements may be carried out at between 200 MHz to about 900 MHz or other suitable frequency. Other frequencies corresponding to a desired operational magnetic field strength may also be employed. Typically, a proton flow probe is installed, as is a temperature controller to maintain the sample temperature at 47+/−0.5° C. The spectrometer 22 is controlled by a digital computer 211 or other signal processing unit. The computer 211 should be capable of performing rapid Fourier transformations. It may also include a data link 212 to another processor or computer 213, and a direct-memory-access channel 214 which can connects to a hard memory storage unit 215.

The digital computer 211 may also include a set of analog-to-digital converters, digital-to-analog converters and slow device I/O ports which connect through a pulse control and interface circuit 216 to the operating elements of the spectrometer 22. These elements include an RF transmitter 217 which produces an RF excitation pulse of the duration, frequency and magnitude directed by at least one digital signal processor that can be onboard or in communication with the digital computer 211, and an RF power amplifier 218 which amplifies the pulse and couples it to the RE transmit coil 219 that surrounds sample cell 220 and/or flow probe 220. The NMR signal produced by the excited sample in the presence of a 9.4 Tesla polarizing magnetic field produced by superconducting magnet 221 is received by a coil 222 and applied to an RF receiver 223. The amplified and filtered NMR signal is demodulated at 224 and the resulting quadrature signals are applied to the interface circuit 216 where they are digitized and input through the digital computer 211. The processor and/or analyzer circuit 20, FIGS. 13 and 14, and/or multiple-parameter MVX risk modules 350, FIGS. 13 and 15, can be located in one or more processors associated with the digital computer 211 and/or in a secondary computer 213 or other computers that may be on-site or remote, accessible via a worldwide network such as the Internet 227.

After the NMR data are acquired from the sample in the measurement cell 220, processing by the computer 211 produces another file that can, as desired, be stored in the storage 215. This second file is a digital representation of the chemical shift spectrum and it is subsequently read out to the computer 213 for storage in its storage 225 or a database associated with one or more servers. Under the direction of a program stored in its memory or accessible by the computer 213, the computer 213, which may be a laptop computer, desktop computer, workstation computer, electronic notepad, electronic tablet, smartphone or other device with at least one processor or other computer, processes the chemical shift spectrum in accordance with the teachings of the present invention to generate a report which may be output to a printer 226 or electronically stored and relayed to a desired email address or URI Those skilled in this art will recognize that other output devices, such as a computer display screen, electronic notepad, smartphone and the like, may also be employed for the display of results.

It should be apparent to those skilled in the art that the functions performed by the computer 213 and its separate storage 225 may also be incorporated into the functions performed by the spectrometer's digital computer 211. In such case, the printer 226 may be connected directly to the digital computer 211. Other interfaces and output devices may also be employed, as are well-known to those skilled in this art.

Certain embodiments of the present invention are directed at providing methods, systems and/or computer program products that use MVX evaluations that may be particularly useful in automated screening tests of clinical disease states and/or risk assessment evaluations for screening of in vitro biosamples.

Embodiments of the present disclosure may take the form of an entirely software embodiment or an embodiment combining software and hardware aspects, all generally referred to herein as a "circuit" or "module."

As will be appreciated by one of skill in the art, the present disclosure may be embodied as an apparatus, a method, data or signal processing system, or computer program product. Accordingly, the present disclosure may take the form of an entirely software embodiment, or an embodiment combining software and hardware aspects. Furthermore, certain embodiments of the present disclosure may take the form of a computer program product on a computer-usable storage medium having computer-usable program code means embodied in the medium. Any suitable computer readable medium may be utilized including hard disks, CD-ROMs, optical storage devices, or magnetic storage devices.

The computer-usable or computer-readable medium may be, but is not limited to, an electronic, magnetic, optical, electromagnetic, infrared, or semiconductor system, apparatus, device, or propagation medium. More specific examples (a non-exhaustive list) of the computer-readable medium would include the following: an electrical connection having one or more wires, a portable computer diskette, a random access memory (RAM), a read-only memory (ROM), an erasable programmable read-only memory (EPROM or Flash memory), an optical fiber, and a portable compact disc read-only memory (CD-ROM). Note that the computer-usable or computer-readable medium could even be paper or another suitable medium, upon which the program is printed, as the program can be electronically captured, via, for instance, optical scanning of the paper or other medium, then compiled, interpreted or otherwise processed in a suitable manner if necessary, and then stored in a computer memory.

Computer program code for carrying out operations of the present disclosure may be written in an object oriented programming language such as Java7, Smalltalk, Python, Labview, C++, or VisualBasic. However, the computer program code for carrying out operations of the present disclosure may also be written in conventional procedural programming languages, such as the "C" programming language or even assembly language. The program code may execute entirely on the user's computer, partly on the user's computer, as a stand-alone software package, partly on the user's computer and partly on a remote computer or entirely on the remote computer. In the latter scenario, the remote computer may be connected to the user's computer through a local area network (LAN) or a wide area network (WAN) or secured area network (SAN), or the connection may be made to an external computer (for example, through the Internet using an Internet Service Provider).

Figure 15:
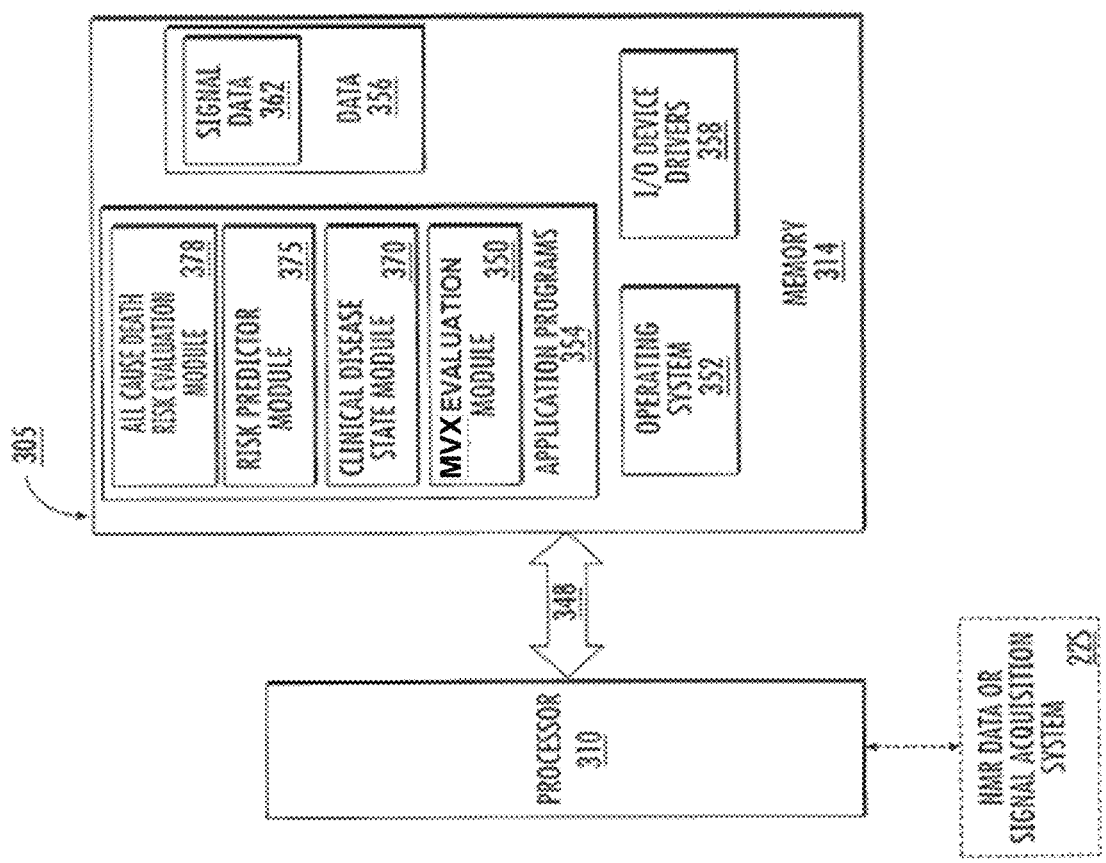
FIG. 15 shows a schematic diagram of a data processing system according to embodiments of the present disclosure.

FIG. 15, is a block diagram of exemplary embodiments of data processing systems 305 that illustrates systems, methods, and computer program products in accordance with embodiments of the present invention. The processor 310 may comprise or communicate with the memory 314 via an address/data bus 348. The processor 310 can be any commercially available or custom microprocessor. The memory 314 is representative of the overall hierarchy of memory devices containing the software and data used to implement the functionality of the data processing system 305. The memory 314 can include, but is not limited to, the following types of devices: cache, ROM, PROM, EPROM, EEPROM, flash memory, SRAM, and DRAM.

As shown in FIG. 15, the memory 314 may include several categories of software and data used in the data processing system 305: the operating system 352; the application programs 354; the input/output (I/O) device drivers 358; a MVX Evaluation Module 350; and the data 356. The MVX Evaluation Module 350 can deconvolve NMR signal to reveal defined NMR signal peak regions in proton NMR spectra of a respective biosample to calculate a MVX value using the various approaches disclosed herein.

The data 356 may include signal (constituent and/or composite spectrum lineshape) data 362 which may be obtained from a data or signal acquisition system 225 (e.g., NMR spectrometer 22 and/or analyzer 22). As will be appreciated by those of skill in the art, the operating system 352 may be any operating system suitable for use with a data processing system, such as OS/2, AIX or OS/390 from International Business Machines Corporation, Armonk, N.Y., WindowsCE, WindowsNT, Windows95, Windows98, Windows2000, WindowsXP, Windows 10 from Microsoft Corporation, Redmond, Wash., PalmOS from Palm, Inc., MacOS from Apple Computer, UNIX, FreeBSD, or Linux, proprietary operating systems or dedicated operating systems, for example, for embedded data processing systems.

The I/O device drivers 358 typically include software routines accessed through the operating system 352 by the application programs 354 to communicate with devices such as I/O data port(s), data storage 356 and certain memory 314 components and/the image acquisition system 225. The application programs 354 are illustrative of the programs that implement the various features of the data processing system 305 and can include at least one application, which supports operations according to embodiments of the present invention. Finally, the data 356 represents the static and dynamic data used by the application programs 354, the operating system 352, the I/O device drivers 358, and other software programs that may reside in the memory 314.

While the present invention is illustrated, for example, with reference to the Module 350 being an application program in FIG. 15, as will be appreciated by those of skill in the art, other configurations may also be utilized while still benefiting from the teachings of the present invention. Thus, the present invention should not be construed as limited to the configuration of FIG. 15, which is intended to encompass any configuration capable of carrying out the operations described herein.

In certain embodiments, the Module 350 includes computer program code for providing a MVX measurement which may be used as a marker to assess a clinical disease state or risk and/or to indicate whether therapy intervention is desired and/or track efficacy of a therapy or even an unintended consequence of a therapy.

Further embodiments of the disclosure will now be described by way of the following non-limiting Examples.

EXAMPLES

Example 1

A Metabolic Vulnerability Index (MVX) mathematical model was developed using data collected from the CATHGEN study population of 6936 participants. Traditional clinical parameters including age, race, gender, smoking status, hypertension status, diabetes status, BMI, triglyceride-rich lipoprotein particles (TRLP), and LDL particles (LDLP) were recorded for each patient. Additionally, measurements of GlycA, S-HDLP, BCAAs, ketone bodies, citrate, and protein were derived from a single nuclear magnetic resonance (NMR) spectrum of a plasma sample from each study participant. A Cox proportional hazards prediction model for mortality was used to generate the predictive strengths ($\chi^2$) and statistical significance (p value) of each parameter, as seen in FIGS. 4 and 5. While, in this case, all the listed parameters were used in the prediction model to generate the predictive strength of each parameter, MVX alone in a model is a very strong, highly statistically significant mortality risk predictor, as seen in FIG. 7.

Using the MVX mathematical model generated from the Cox proportional hazards prediction model for mortality, MVX score (1-100) values were generated for each participant in the CATHGEN study. These MVX scores were then used to subdivide the population into 9 subgroups, with the cumulative mortality incidence of each subgroup over the 5-year follow-up period shown to increase in direct proportion to increased MVX score, as seen in FIG. 3.

FIG. 16 provides an example of how the various models for INFX, MMX1, MMX2 and MMX can be used to develop numerical scores such as those shown in FIG. 3. For application to normal (i.e., not high-risk) populations, MVX1=(INFX*0.84310)+(MMX1*1.0), where MMX1=10+(lnBCAA*−1.10056)+(lnKetoneBody*0.2373). In contrast, for high risk populations, the contribution of MMX includes MMX1 and MMX2 (FIG. 16). The actual coefficients used (e.g., for MMX1, 34=−1.10056 and 135=0.2373) may vary depending upon the populations used and/or the analysis performed.

EMBODIMENTS

A1. A method of determining the levels of markers associated with a subject's relative risk of premature death comprising:
obtaining a sample from the subject; and
measuring GlycA, at least one high density lipoprotein particle (HDLP) subclass, at least one branched chain amino acid (BCAA), and at least one ketone body (KetoneBody).
A2. The method of A1, wherein the measurement of the GlycA, the at least one HDLP subclass, the at least one BCAA, and the at least one ketone body are used to generate a metabolic vulnerability index (MVX) value.

A3. The method of A1-A2, wherein the HDLP subclass is small HDLP (S-HDLP).

A4. The method of A2-A3, wherein the MVX value is determined using the following model: MVX=A+β1*lnGlycA+β2*lnS-HDLP+β4*lnBCAA+β5*lnKetoneBody.

A5. The method of A2-A3, wherein the MVX value is determined using the following model: MVX=A+β1*lnGlycA+β2*lnS-HDLP+β3*(lnGlycA*lnS-HDLP)+β4*lnBCAA+β5*lnKetoneBody.

A6. The method of A5, wherein the MVX value is determined in a subject deemed to be at low-risk for a cardiovascular event.

A7. The method of A1-A2, further comprising measuring at least one of citrate (Citrate) and serum protein (Protein).

A8. The method of A7, wherein the measuring of at least one of citrate and serum protein is performed in a subject deemed to be at high risk for CVD related death.

A9. The method of A7-A8, wherein the MVX value is determined using the following model: MVX=A+β1*lnGlycA+β2*lnS-HDLP+β3*(lnGlycA*lnS-HDLP)+β4*lnBCAA+β5*lnKetoneBody+β6*lnCitrate+β7*lnProtein+β8*(lnCitrate*lnProtein).

A10. The method of any one of the prior embodiments, wherein the MVX value is defined as comprising an inflammation index (INFX) value and a metabolic malnutrition index (MMX) value.

A11. The method of A10, wherein the measurement of GlycA and the at least one HDLP subclass are used to generate an inflammation index (INFX) value.

A12. The method of A10-A11, wherein the INFX value is determined using the following model: INFX=β1*lnGlycA+β2*lnS-HDLP+β3*(lnGlycA*lnS-HDLP).

A13. The method of A10, wherein the measurement of the at least one BCAA and the at least one ketone body, and optionally protein and citrate, are used to generate the metabolic malnutrition index (MMX) value.

A14. The method of A10 and A13, wherein the metabolic malnutrition index (MMX) value is defined as: MMX=β4*lnBCAA+β5*lnKetoneBody+β6*lnCitrate+β7*lnProtein+β8*(lnCitrate*lnProtein).

A15. The method of any one of A10, A13 and A14 wherein the metabolic malnutrition index (MMX) comprises a first metabolic malnutrition index MMX1 value and a second metabolic malnutrition index MMX2 value.

A16. The method of A15, wherein MMX=β9*MMX1+β10*MMX2.

A17. The method of A15-A16, wherein MMX1=β4*lnBCAA+β5*lnKetoneBody.

A18. The method of A15-A16, wherein MMX2=β6*lnCitrate+β7*lnProtein+β8*(lnCitrate*lnProtein).

A19. The method of any one of A15-A17, wherein the MVX value is determined using the following model: MVX1=βi*INFX+βm*MMX1.

A20. The method of A19, wherein MVX1 is determined for subjects deemed to be at low risk for a CVD related event.

A21. The method of A15 wherein the MVX value is determined using the following model: MVX=βi*INFX+βm*MMX, wherein MMX=β9*MMX1+β10*MMX2.

A22. The method of A21, wherein MVX is determined for subjects deemed to be at high-risk for a CVD related event.

A23. The method of any one of the prior embodiments, wherein the BCAA is at least one of leucine, isoleucine, or valine.

A24. The method of any one of the prior embodiments, wherein the ketone bodies are at least one of acetone, acetoacetate, or beta-hydroxybutyrate.

A25. The method of any one of the prior embodiments, wherein the measuring is performed by NMR.

B1. A method of determining the levels of markers associated with a subject's relative risk of premature death comprising:
obtaining a sample from the subject;
measuring GlycA, at least one high density lipoprotein particle (HDLP) subclass, at least one branched chain amino acid (BCAA), and at least one ketone body (KetoneBody) and optionally at least one of citrate (Citrate) and serum protein (Protein);
using the measurement of GlycA and the at least one HDLP subclass to generate an inflammation index (INFX) value;
using the measurement of the at least one BCAA and the at least one ketone body, and optionally, the Protein and Citrate, to generate at least one metabolic malnutrition index (MMX) value; and
determining a metabolic vulnerability index (MVX) value based on the INFX and MMX values.

B2. The method of B1, wherein the HDLP subclass is small HDLP (S-HDLP).

B3. The method of B1-B2, wherein the INFX value is determined using the following model: INFX=β1*lnGlycA+β2*lnS-HDLP+β3*(lnGlycA*lnS-HDLP).

B4. The method of B1-B2, wherein the metabolic malnutrition index (MMX) value is defined as: MMX=β4*lnBCAA+β5*lnKetoneBody+β6*lnCitrate+β7*lnProtein+β8*(lnCitrate*lnProtein).

B5. The method of any one of embodiments B1-B4, wherein the metabolic malnutrition index (MMX) comprises a first metabolic malnutrition index MMX1 value and a second metabolic malnutrition index MMX2 value.

B6. The method of B5, wherein MMX=β9*MMX1+β10*MMX2.

B7. The method of B5-B6, wherein MMX1=β4*lnBCAA+β5*lnKetoneBody.

B8. The method of B5-B6, wherein MMX2=β6*lnCitrate+β7*lnProtein+β8*(lnCitrate*lnProtein).

B9. The method of B5-B7, wherein the MVX value is determined using the following model: MVX1=βi*INFX+βm*MMX1.

B10. The method of B9, wherein MVX1 is determined for subjects deemed to be at low risk for a CVD related event.

B11. The method of any one of B5-B8 wherein the MVX value is determined using the following model: MVX=βi*INFX+βm*MMX, wherein MMX=β9*MMX1+β10*MMX2.

B12. The method of B11, wherein MVX is determined for subjects deemed to be at high-risk for a CVD related event.

B13. The method of any one of B1-B12, wherein the BCAA is at least one of leucine, isoleucine, or valine.

B14. The method of any one of B1-B13, wherein the ketone bodies are at least one of acetone, acetoacetate, or beta-hydroxybutyrate.

B15. The method of any one of B1-B14, wherein the measuring is performed by NMR.

C1. A system to perform any one of the previous embodiments.

D1. A system comprising:
an NMR spectrometer configured to acquire an NMR spectrum and/or spectra comprising at least one signal for GlycA, at least one signal for at least one high density lipoprotein particle (HDLP) subclass, at least one signal for at least one branched chain amino acid (BCAA), and at least one signal for at least one ketone body (KetoneBody); and a processor to determine a metabolic vulnerability index (MVX) value based on the measured at least one signal for the GlycA, the at least one high density lipoprotein particle (HDLP) subclass, the at least one branched chain amino acid (BCAA), and the at least one ketone body (KetoneBody) wherein the processor comprises or communicates with a memory.

D2. The system of D1, further comprising an NMR spectrometer configured to acquire an NMR spectrum and/or spectra comprising at least one signal for serum protein (Protein) and/or citrate (Citrate); and a processor to determine a metabolic vulnerability index (MVX) value based on the measured at least one signal for the serum protein (Protein) and the citrate (Citrate).

D3. The system of D1-D2, wherein the HDLP subclass is small HDLP (S-HDLP).

D4. The system of any one of D1 or D3, wherein the processor is further configured to calculate an MVX score based on the measurements of GlycA, at least one ketone body, at least one branched chain amino acid, and the at least one of the HDLP subclass using the following formula: MVX=A+β1*lnGlycA+β2*lnS-HDLP+β4*lnBCAA+β5*lnKetoneBody D5. The system of any one of D1 or D3, wherein the processor is further configured to calculate an MVX score using the following model: MVX=A+β1*lnGlycA+β2*lnS-HDLP+β3*(lnGlycA*lnS-HDLP)+β4*lnBCAA+β5*lnKetoneBody.

D6. The system of any one of D1-D3, wherein the processor is further configured to calculate an MVX value using the following model: MVX=A+β1*lnGlycA+β2*lnS-HDLP+β3*(lnGlycA*lnS-HDLP)+β4*lnBCAA+β5*lnKetoneBody+β6*lnCitrate+β7*lnProtein+β8*(lnCitrate*lnProtein).

D7. The system of any one of D1-D6, wherein the processor is further configured to calculate an MVX value comprising an inflammation index (INFX) value and a metabolic malnutrition index (MMX value).

D8. The system of D7, wherein the processor is further configured to calculate an INFX value using the following model: INFX=β1*lnGlycA+β2*lnS-HDLP+β3*(lnGlycA*lnS-HDLP).

D9. The system of D7, wherein the processor is further configured to calculate an MMX value using the following model: MMX=β4*lnBCAA+β5*lnKetoneBody+β6*lnCitrate+β7*lnProtein+β8*(lnCitrate*lnProtein).

D10. The system of any one of D7-D9, wherein the processor is further configured to calculate a metabolic malnutrition index (MMX) comprising a first metabolic malnutrition index MMX1 value and a second metabolic malnutrition index MMX2 value.

D11. The system of D10, wherein the processor is further configured to calculate an MMX value using the following model: MMX=β9*MMX1+β10*MMX2.

D12. The system of D10-D11, wherein the processor is further configured to calculate an MMX1 value using the following model: MMX1=β4*lnBCAA+β5*lnKetoneBody.

D13. The system of D10-D11, wherein the processor is further configured to calculate an MMX2 value using the following model: MMX2=β6*lnCitrate+β7*lnProtein+β8*(lnCitrate*lnProtein).

D14. The system of any one of D10-D12, wherein the processor is further configured to calculate an MVX value using the following model: MVX1=βi*INFX+βm*MMX1.

D15. The system of any one of D10 or D11-D13, wherein the processor is further configured to calculate an MVX value using the following model: MVX=βi*INFX+βm*MMX, wherein MMX=β9*MMX1+β10*MMX2.

D16. The system of any one of D1-D15, wherein the BCAA is at least one of leucine, isoleucine, or valine.

D17. The system of any one of D1-D16, wherein the ketone bodies are at least one of acetone, acetoacetate, or beta-hydroxybutyrate.

E1. An NMR system comprising:
an NMR spectrometer;
a flow probe in communication with the spectrometer; and
a processor in communication with the spectrometer configured to obtain (i) at least one NMR signal of a defined GlycA fitting region of NMR spectra associated with GlycA of a blood plasma or serum specimen in the flow probe; (ii) at least one NMR signal of a defined ketone body fitting region of NMR spectra associated with the specimen in the flow probe; (iii) at least one NMR signal of a defined BCAA fitting region of NMR spectra associated with the specimen in the flow probe; and, (iv) at least one NMR signal for at least one HDLP subclass fitting region of NMR spectra associated with the specimen in the flow probe; and optionally, at least one NMR signal for serum protein (Protein) and/or citrate (Citrate) fitting region(s) of NMR spectra associated with the specimen in the flow probe E2. The system of E1, wherein the HDLP subclass is small HDLP (S-HDLP).

E3. The system of E1-E2, wherein the processor is further configured to calculate an MVX score based on the measurements of GlycA, at least one ketone body, at least one branched chain amino acid, and the at least one of the HDLP subclass using the following formula: MVX=A+β1*lnGlycA+β2*lnS-HDLP+β4*lnBCAA+β5*lnKetoneBody E4. The system of E1-E2, wherein the processor is further configured to calculate an MVX score using the following model: MVX=A+β1*lnGlycA+β2*lnS-HDLP+β3*(lnGlycA*lnS-HDLP)+β4*lnBCAA+β5*lnKetoneBody.

E5. The system of any one of E1-E4, wherein the processor is further configured to calculate an MVX value using the following model: MVX=A+β1*lnGlycA+β2*lnS-HDLP+β3*(lnGlycA*lnS-HDLP)+β4*lnBCAA+β5*lnKetone- Body+β6*lnCitrate+β7*lnProtein+β8*(lnCitrate*lnProtein).

E6. The system of any one of E1-E5, wherein the processor is further configured to calculate an MVX value comprising an inflammation index (INFX) value and a metabolic malnutrition index (MMX value).

E7. The system of E6, wherein the processor is further configured to calculate an INFX value using the following model: INFX=β1*lnGlycA+β2*lnS-HDLP+β3*(lnGlycA*lnS-HDLP).

E8. The system of E6, wherein the processor is further configured to calculate an MMX value using the following model: MMX=β4*lnBCAA+β5*lnKetoneBody+β6*lnCitrate+β7*lnProtein+β8*(lnCitrate*lnProtein).

E9. The system of any one of E6-E7, wherein the processor is further configured to calculate a metabolic malnutrition index (MMX) comprising a first metabolic malnutrition index MMX1 value and a second metabolic malnutrition index MMX2 value.

E10. The system of E9, wherein the processor is further configured to calculate an MMX value using the following model: MMX=β9*MMX1+β10*MMX2.

E11. The system of E9-E10, wherein the processor is further configured to calculate an MMX1 value using the following model: MMX1=$\beta 4$*lnBCAA+$\beta 5$*lnKetoneBody.

E12. The system of E9-E10, wherein the processor is further configured to calculate an MMX2 value using the following model: MMX2=$\beta 6$*lnCitrate+$\beta 7$*lnProtein+$\beta 8$*(lnCitrate*lnProtein).

E13. The system of any one of E9-E11, wherein the processor is further configured to calculate an MVX value using the following model: MVX1=$\beta i$*INFX+$\beta m$*MMX1.

E14. The system of any one of E10-E13, wherein the processor is further configured to calculate an MVX value using the following model: MVX=$\beta i$*INFX+$\beta m$*MMX, wherein MMX=$\beta 9$*MMX1+$\beta 10$*MMX2.

E15. The system of any one of E1-E14, wherein the BCAA is at least one of leucine, isoleucine, or valine.

E16. The system of any one of E1-E15, wherein the ketone bodies are at least one of acetone, acetoacetate, or beta-hydroxybutyrate.

F1. A method of monitoring a patient comprising:
obtaining a sample from the subject;
measuring GlycA, at least one high density lipoprotein particle (HDLP) subclass, at least one branched chain amino acid (BCAA), and at least one ketone body (KetoneBody) and optionally, at least one of citrate (Citrate) and/or serum protein (Protein) in the sample;
determining a metabolic vulnerability index (MVX) value based on the measurements; and
evaluating at least whether the MVX value is above a defined level of a population norm associated with increased risk of all-cause mortality.

F2. The method of F1, wherein the HDLP subclass is small HDLP (S-HDLP).

F3. The method of F1-F2, wherein the MVX value is determined using the following model: MVX=A+$\beta 1$*lnGlycA+$\beta 2$*lnS-HDLP+$\beta 4$*lnBCAA+$\beta 5$*lnKetoneBody.

F4. The method of F1-F2, wherein the MVX value is determined using the following model: MVX=A+$\beta 1$*lnGlycA+$\beta 2$*lnS-HDLP+$\beta 3$*(lnGlycA*lnS-HDLP)+$\beta 4$*lnBCAA+$\beta 5$*lnKetoneBody.

F5. The method of F1-F4, wherein the MVX value is determined in a subject deemed to be at low-risk for a cardiovascular event.

F6. The method of F1, wherein the measuring of at least one of citrate and serum protein is performed in a subject deemed to be at high risk for CVD related death.

F7. The method of F1-F2, wherein the MVX value is determined using the following model: MVX=A+$\beta 1$*lnGlycA+$\beta 2$*lnS-HDLP+$\beta 3$*(lnGlycA*lnS-HDLP)+$\beta 4$*lnBCAA+$\beta 5$*lnKetoneBody+$\beta 6$*lnCitrate+$\beta 7$*lnProtein+$\beta 8$*(lnCitrate*lnProtein).

F8. The method of F1-F7, wherein the MVX value is defined as comprising an inflammation index (INFX) value and a metabolic malnutrition index (MMX) value.

F9. The method of F8, wherein the measurement of GlycA and the at least one HDLP subclass are used to generate an inflammation index (INFX) value.

F10. The method of F8-F9, wherein the INFX value is determined using the following model: INFX=$\beta 1$*lnGlycA+$\beta 2$*lnS-HDLP+$\beta 3$*(lnGlycA*lnS-HDLP).

F11. The method of F8, wherein the measurement of the at least one BCAA and the at least one ketone body, and optionally protein and citrate, are used to generate the metabolic malnutrition index (MMX) value.

F12. The method of any one of F8 or F11, wherein the metabolic malnutrition index (MMX) value is defined as: MMX=$\beta 4$*lnBCAA+$\beta 5$*lnKetoneBody+$\beta 6$*lnCitrate+$\beta 7$*lnProtein+$\beta 8$*(lnCitrate*lnProtein).

F13. The method of any one of F8 or F11 wherein the metabolic malnutrition index (MMX) comprises a first metabolic malnutrition index MMX1 value and a second metabolic malnutrition index MMX2 value.

F14. The method of F13, wherein MMX=$\beta 9$*MMX1+$\beta 10$*MMX2.

F15. The method of any one of F13 or F14, wherein MMX1=$\beta 4$*lnBCAA+$\beta 5$*lnKetoneBody.

F16. The method of any one of F13 of F14, wherein MMX2=$\beta 6$*lnCitrate+$\beta 7$*lnProtein+$\beta 8$*(lnCitrate*lnProtein).

F17. The method of any one of F13-F15, wherein the MVX value is determined using the following model: MVX1=$\beta i$*INFX+$\beta m$*MMX1.

F18. The method of F17, wherein MVX1 is determined for subjects deemed to be at low risk for a CVD related event.

F19. The method of F13 wherein the MVX value is determined using the following model: MVX=$\beta i$*INFX+$\beta m$*MMX, wherein MMX=$\beta 9$*MMX1+$\beta 10$*MMX2.

F20. The method of F19, wherein MVX is determined for subjects deemed to be at high-risk for a CVD related event.

F21. The method of any one of F1-F20, wherein the BCAA is at least one of leucine, isoleucine, or valine.

F22. The method of any one of F1-F21, wherein the ketone bodies are at least one of acetone, acetoacetate, or beta-hydroxybutyrate.

F23. The method of any one of F1-F21, wherein the measuring is performed by NMR.

G1. A method of monitoring a patient comprising:
(a) obtaining a sample from the subject;
(b) measuring GlycA, at least one high density lipoprotein particle (HDLP) subclass, at least one branched chain amino acid (BCAA), and at least one ketone body (KetoneBody) and optionally at least one of citrate (Citrate) and serum protein (Protein) in the sample;
(c) determining a metabolic vulnerability index (MVX) value based on the measurements;
(d) repeating steps (a)-(c) at a later time point; and
(e) evaluating at least whether the MVX value has increased or decreased over time.

G2. The method of G1, wherein the HDLP subclass is small HDLP (S-HDLP).

G3. The method of G1-G2, wherein the MVX value is determined using the following model: MVX=A+$\beta 1$*lnGlycA+$\beta 2$*lnS-HDLP+$\beta 4$*lnBCAA+$\beta 5$*lnKetoneBody.

G4. The method of G1-G2, wherein the MVX value is determined using the following model: MVX=A+$\beta 1$*lnGlycA+$\beta 2$*lnS-HDLP+$\beta 3$*(lnGlycA*lnS-HDLP)+$\beta 4$*lnBCAA+$\beta 15$*lnKetoneBody.

G5. The method of any one of G1-G4, wherein the MVX value is determined in a subject deemed to be at low-risk for a cardiovascular event.

G6. The method of G1-G2, wherein the measuring of at least one of citrate and serum protein is performed in a subject deemed to be at high risk for CVD related death.

G7. The method of any one of G1, G2, or G6 wherein the MVX value is determined using the following model: MVX=A+$\beta 1$*lnGlycA+$\beta 2$*lnS-HDLP+$\beta 3$*(lnGlycA*lnS-HDLP)+$\beta 4$*lnBCAA+$\beta 5$*lnKetoneBody+$\beta 6$*lnCitrate+$\beta 7$*lnProtein+$\beta 8$*(lnCitrate*lnProtein).

G8. The method of any one of G1-G7, wherein the MVX value is defined as comprising an inflammation index (INFX) value and a metabolic malnutrition index (MMX) value.

G9. The method of G8, wherein the measurement of GlycA and the at least one HDLP subclass are used to generate an inflammation index (INFX) value.

G10. The method of G8-G9, wherein the INFX value is determined using the following model: INFX=β1*lnGlycA+β2*lnS-HDLP+β3*(lnGlycA*lnS-HDLP).

G11. The method of G8, wherein the measurement of the at least one BCAA and the at least one ketone body, and optionally protein and citrate, are used to generate the metabolic malnutrition index (MMX) value.

G12. The method of any one of G8 or G11, wherein the metabolic malnutrition index (MMX) value is defined as: MMX=β4*lnBCAA+β5*lnKetoneBody+β6*lnCitrate+β7*lnProtein+β8*(lnCitrate*lnProtein).

G13. The method of any one of G8, G11 or G12 wherein the metabolic malnutrition index (MMX) comprises a first metabolic malnutrition index MMX1 value and a second metabolic malnutrition index MMX2 value.

G14. The method of G13, wherein MMX=β9*MMX1+β10*MMX2.

G15. The method of G13, wherein MMX1=β4*lnBCAA+β5*lnKetoneBody.

G16. The method of G13, wherein MMX2=β6*lnCitrate+β7*lnProtein+β8*(lnCitrate*lnProtein).

G17. The method of G15, wherein the MVX value is determined using the following model: MVX1=βi*INFX+βm*MMX1.

G18. The method of G17 wherein MVX1 is determined for subjects deemed to be at low risk for a CVD related event.

G19. The method of G13 wherein the MVX value is determined using the following model: MVX=βi*INFX+βm*MMX, wherein MMX=β9*MMX1+β10*MMX2.

G20. The method of G19, wherein MVX is determined for subjects deemed to be at high-risk for a CVD related event.

G21. The method of any one of G1-G20, wherein the BCAA is at least one of leucine, isoleucine, or valine.

G22. The method of any one of G1-21, wherein the ketone bodies are at least one of acetone, acetoacetate, or beta-hydroxybutyrate.

G23. The method of G1, wherein the measuring is performed by NMR.

The foregoing is illustrative of the present disclosure and is not to be construed as limiting thereof. Although a few exemplary embodiments of this disclosure have been described, those skilled in the art will readily appreciate that many modifications are possible in the exemplary embodiments without materially departing from the novel teachings and advantages of this disclosure. Accordingly, all such modifications are intended to be included within the scope of this disclosure as defined in the claims. In the claims, means-plus-function clauses, where used, are intended to cover the structures described herein as performing the recited function and not only structural equivalents but also equivalent structures. Therefore, it is to be understood that the foregoing is illustrative of the present disclosure and is not to be construed as limited to the specific embodiments disclosed, and that modifications to the disclosed embodiments, as well as other embodiments, are intended to be included within the scope of the appended claims. The disclosure is defined by the following claims, with equivalents of the claims to be included therein.

That which is claimed is:

1. A method of determining the levels of markers associated with a subject's relative risk of premature death comprising:

obtaining a sample from the subject; and measuring GlycA, at least one high density lipoprotein particle (HDLP) subclass, at least one branched chain amino acid (BCAA), and at least one ketone body (KetoneBody), wherein the measurement of the GlycA, the at least one HDLP subclass, the at least one BCAA, and the at least one ketone body are used to generate a metabolic vulnerability index (MVX) value.

2. The method of claim 1, wherein the HDLP subclass is small HDLP (S-HDLP).

3. The method of claim 2, wherein the MVX value is determined using the following model: MVX=A+β1*lnGlycA+β2*lnS-HDLP+β4*lnBCAA+β5*lnKetoneBody.

4. The method of claim 2, wherein the MVX value is determined using the following model: MVX=A+β1*lnGlycA+β2*lnS-HDLP+β3*(lnGlycA*lnS-HDLP)+β4*lnBCAA+β5*lnKetoneBody.

5. The method of claim 4, wherein the MVX value is determined in a subject deemed to be at low-risk for a cardiovascular event.

6. The method of claim 1, further comprising measuring at least one of citrate (Citrate) and serum protein (Protein).

7. The method of claim 6, wherein the measuring of at least one of citrate and serum protein is performed in a subject deemed to be at high risk for CVD related death.

8. The method of claim 6, wherein the MVX value is determined using the following model: MVX=A+β1*lnGlycA+β2*lnS-HDLP+(β3*(lnGlycA*lnS-HDLP)+β4*lnBCAA+β5*lnKetoneBody+β6*lnCitrate+β7*lnProtein+β8*(lnCitrate*lnProtein).

9. The method of claim 1, wherein the MVX value is defined as comprising an inflammation index (INFX) value and a metabolic malnutrition index (MMX) value.

10. The method of claim 9, wherein the measurement of GlycA and the at least one HDLP subclass are used to generate an inflammation index (INFX) value.

11. The method of claim 9, wherein the INFX value is determined using the following model: INFX=β1*lnGlycA+β2*lnS-HDLP+β3*(lnGlycA*lnS-HDLP).

12. The method of claim 9, wherein the measurement of the at least one BCAA and the at least one ketone body, and optionally protein and citrate, are used to generate the metabolic malnutrition index (MMX) value.

13. The method of claim 9, wherein the metabolic malnutrition index (MMX) value is defined as: MMX=β4*lnBCAA+β5*lnKetoneBody+β6*lnCitrate+β7*lnProtein+β8*(lnCitrate*lnProtein).

14. The method of claim 9 wherein the metabolic malnutrition index (MMX) comprises a first metabolic malnutrition index MMX1 value and a second metabolic malnutrition index MMX2 value.

15. The method of claim 14, wherein MMX=β9*MMX1+β10*MMX2.

16. The method of claim 14, wherein MMX1=β4*lnBCAA+β5*lnKetoneBody.

17. The method of claim 14, wherein MMX2=β6*lnCitrate+β7*lnProtein+β8*(lnCitrate*lnProtein).

18. The method of claim 14, wherein the MVX value is determined using the following model: MVX1=βi*INFX+βm*MMX1.

19. The method of claim 18, wherein MVX1 is determined for subjects deemed to be at low risk for a CVD related event.

20. The method of claim 14 wherein the MVX value is determined using the following model: MVX=βi*INFX+βm*MMX, wherein MMX=β9*MMX1+β10*MMX2.

21. The method of claim 20, wherein MVX is determined for subjects deemed to be at high-risk for a CVD related event.

22. The method of claim 1, wherein the BCAA is at least one of leucine, isoleucine, or valine.

23. The method of claim 1, wherein the ketone bodies are at least one of acetone, acetoacetate, or beta-hydroxybutyrate.

24. The method of claim 1, wherein the measuring is performed by NMR.

25. A system comprising:
   an NMR spectrometer configured to acquire an NMR spectrum and/or spectra comprising at least one signal for GlycA, at least one signal for at least one high density lipoprotein particle (HDLP) subclass, at least one signal for at least one branched chain amino acid (BCAA), and at least one signal for at least one ketone body (KetoneBody); and
   a processor to determine a metabolic vulnerability index (MVX) value based on the measured at least one signal for the GlycA, the at least one high density lipoprotein particle (HDLP) subclass, the at least one branched chain amino acid (BCAA), and the at least one ketone body (KetoneBody)
   wherein the processor comprises or communicates with a memory.

26. The system of claim 25, wherein the NMR spectrometer is further configured to acquire an NMR spectrum and/or spectra comprising at least one signal for serum protein (Protein) and/or citrate (Citrate); and
   the processor to further determines the MVX value based on the measured at least one signal for the serum protein (Protein) and the citrate (Citrate).

27. A method of monitoring a patient comprising:
   (a) obtaining a sample from the subject;
   (b) measuring GlycA, at least one high density lipoprotein particle (HDLP) subclass, at least one branched chain amino acid (BCAA), and at least one ketone body (KetoneBody) and optionally at least one of citrate (Citrate) and serum protein (Protein) in the sample;
   (c) determining a metabolic vulnerability index (MVX) value based on the measurements;
   (d) repeating steps (a)-(c) at a later time point; and
   (e) evaluating at least whether the MVX value has increased or decreased over time.

28. The method of claim 27, wherein the HDLP subclass is small HDLP (S-HDLP).

29. The method of claim 27, wherein the measuring is performed by NMR.

* * * * *